United States Patent
Woolfson et al.

(10) Patent No.: US 9,562,074 B2
(45) Date of Patent: Feb. 7, 2017

(54) SELF-ASSEMBLING PEPTIDE CAGES FROM COILED-COIL PEPTIDE MODULES

(71) Applicant: The University of Bristol, Bristol (GB)

(72) Inventors: Dek Woolfson, Bristol (GB); Paula Booth, Bristol (GB); Jordan Fletcher, Bristol (GB); Richard Sessions, Bristol (GB); Noah Linden, Bristol (GB)

(73) Assignee: The University of Bristol, Bristol (GB)

( * ) Notice: Subject to any disclaimer, the term of this patent is extended or adjusted under 35 U.S.C. 154(b) by 0 days.

(21) Appl. No.: 14/783,885

(22) PCT Filed: Apr. 11, 2014

(86) PCT No.: PCT/GB2014/051140
§ 371 (c)(1),
(2) Date: Oct. 12, 2015

(87) PCT Pub. No.: WO2014/167350
PCT Pub. Date: Oct. 16, 2014

(65) Prior Publication Data
US 2016/0090401 A1  Mar. 31, 2016

(30) Foreign Application Priority Data

Apr. 11, 2013 (GB) .................................. 1306634.5

(51) Int. Cl.
| | | |
|---|---|---|
| *C07K 14/00* | (2006.01) | |
| *C07K 7/08* | (2006.01) | |
| *A61K 39/08* | (2006.01) | |
| *A61K 39/385* | (2006.01) | |
| *A61K 47/48* | (2006.01) | |
| *B82Y 30/00* | (2011.01) | |
| *B82Y 40/00* | (2011.01) | |
| *A61K 39/00* | (2006.01) | |

(52) U.S. Cl.
CPC .............. *C07K 14/001* (2013.01); *A61K 39/08* (2013.01); *A61K 39/385* (2013.01); *A61K 47/48246* (2013.01); *C07K 7/08* (2013.01); *A61K 2039/6031* (2013.01); *B82Y 30/00* (2013.01); *B82Y 40/00* (2013.01)

(58) Field of Classification Search
None
See application file for complete search history.

(56) References Cited

U.S. PATENT DOCUMENTS 5,712,366 A   1/1998  McGrath et al.

FOREIGN PATENT DOCUMENTS

| WO | 2011/046521 A1 | 4/2011 |
| WO | 2013/052015 A1 | 4/2013 |

OTHER PUBLICATIONS

Yoshizumi et al. "Designed Coiled Coils Promote Folding of a Recombinant Bacterial Collagen," The Journal of Biological Chemistry vol. 286, No. 20, pp. 17512-17520.*
Zaccai et al. "A de novo peptide hexamer with a mutable channel," Nature Chemical Biology | vol. 7 | Dec. 2011, pp. 935-941.*
Chen et al. "Design of an in vivo cleavable disulfide linker in recombinant fusion proteins," BioTechniques, 2010, vol. 49, pp. 513-518.*
International Search Report mailed Jul. 15, 2014 (PCT/GB2014/051140); ISA/EP.
J E Padilla et al: "Nanohedra: Using symmetry to design self-assembling protein cages, layers, crystals and filaments", Proceedings of the National Academy of Sciences, vol. 98, No. 5, May 27, 2001.
S Raman et al: "Structure-based design of peptides that self-assemble into regular polyhedral nanoparticles", Nanomedicine: Nanotechnology, Biology, and Medicine, vol. 2, No. 1, 2006.
E H C Bromley et al: "Designated alpha-helical tectons for constructing multicomponent synthetic biological systems", Journal of the American Chemical Society, vol. 1313, No. 3, 2009.
J M Fletcher et al: "A basis set of de novo coiled coil peptide oligomers for rational protein design and synthetic biology", ACS Chemical Biology, vol. 1, May 4, 2012.
J M Fletcher et al: "Self-assembling cages from coiled-coil peptide modules", Science, vol. 340, Apr. 11, 2013.

* cited by examiner

*Primary Examiner* — Christina Bradley
(74) *Attorney, Agent, or Firm* — Banner & Witcoff, LTD.

(57) ABSTRACT

This invention relates to protein structures, to methods of producing those protein structures, and to peptides used in the formation of the protein structures.

35 Claims, 6 Drawing Sheets

SEQUENCE LISTING

```
<160> NUMBER OF SEQ ID NOS: 23

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Gly Glu Ile Ala Ala Ile Lys Lys Glu Ile Ala Ala Ile Lys Cys Glu
1               5                   10                  15

Ile Ala Ala Ile Lys Gln Gly Tyr Gly
            20                  25

<210> SEQ ID NO 2
<211> LENGTH: 32
<212> TYPE: PRT
<213> ORGANISM: Artificial Sequence
<220> FEATURE:
<223> OTHER INFORMATION: Synthetic Construct

<400> SEQUENCE: 2

Gly Glu Leu Ala Ala Ile Lys Gln Glu Leu Ala Ala Ile Lys Lys Glu
1               5                   10                  15

Leu Ala Ala Ile Lys Cys Glu Leu Ala Ala Ile Lys Gln Gly Ala Gly
            20                  25                  30

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Gly Glu Ile Ala Ala Leu Glu Lys Glu Asn Ala Ala Leu Glu Cys Glu
1               5                   10                  15

Ile Ala Ala Leu Glu Gln Gly Trp Trp
            20                  25
```

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Gly Lys Ile Ala Ala Leu Lys Lys Lys Asn Ala Ala Leu Lys Cys Lys
1               5                   10                  15

Ile Ala Ala Leu Lys Gln Gly Tyr Trp
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic Construct

<400> SEQUENCE: 5

Gly Glu Ile Ala Ala Leu Glu Lys Glu Ile Ala Ala Leu Glu Cys Glu
1               5                   10                  15

Ile Ala Ala Leu Glu Gln Gly Trp Trp
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

Gly Lys Ile Ala Ala Leu Lys Lys Lys Ile Ala Ala Leu Lys Cys Lys
1               5                   10                  15

Ile Ala Ala Leu Lys Gln Gly Tyr Trp
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Gly Glu Ile Ala Ala Ile Lys Gln Glu Ile Ala Ala Ile Lys Cys Glu
1               5                   10                  15

Ile Ala Ala Ile Lys Gln Gly Tyr Gly
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Gly Glu Ile Ala Ala Leu Glu Gln Glu Asn Ala Ala Leu Glu Cys Glu
1               5                   10                  15

Ile Ala Ala Leu Glu Gln Gly Trp Trp
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Gly Lys Ile Ala Ala Leu Lys Gln Lys Asn Ala Ala Leu Lys Cys Lys
1               5                   10                  15

Ile Ala Ala Leu Lys Gln Gly Tyr Trp
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Construct

<400> SEQUENCE: 10

Gly Glu Leu Lys Ala Ile Ala Gln Glu Leu Lys Ala Ile Ala Lys Glu
1               5                   10                  15

Leu Lys Ala Ile Ala Trp Glu Asp Lys Ala Ile Ala Gln Gly Ala Gly
            20                  25                  30

Tyr

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct

<400> SEQUENCE: 11

Gly Glu Leu Lys Ala Ile Ala Gln Glu Leu Lys Ala Ile Ala Lys Glu
1               5                   10                  15

Leu Lys Ala Ile Ala Trp Glu His Lys Ala Ile Ala Gln Gly Ala Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic Construct

<400> SEQUENCE: 12

Gly Glu Ile Ala Ala Ile Glu Gln Glu Ile Ala Ala Asn Lys Lys Glu
1               5                   10                  15

Ile Ala Ala Ile Lys Trp Lys Ile Ala Ala Ile Lys Gln Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic Construct

<400> SEQUENCE: 13

Gly Lys Ile Ala Ala Ile Lys Gln Glu Ile Ala Ala Asn Glu Lys Glu
1               5                   10                  15

-continued

Ile Ala Ala Ile Lys Trp Glu Ile Ala Ile Lys Gln Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct

<400> SEQUENCE: 14

Gly Glu Ile Ala Ala Ile Lys Gln Lys Ile Ala Ala Asn Lys Lys Glu
1               5                   10                  15

Ile Ala Ala Ile Lys Trp Glu Ile Ala Ala Ile Glu Gln Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic Construct

<400> SEQUENCE: 15

Lys Lys Lys Lys Gly Gly Gly Glu Ile Ala Ala Ile Lys Lys Glu Ile
1               5                   10                  15

Ala Ala Ile Lys Cys Glu Ile Ala Ala Ile Lys Gln Gly Tyr Gly
            20                  25                  30

<210> SEQ ID NO 16
<211> LENGTH: 27
<212> TYPE: PRT
<213> ORGANISM: Artificial Sequence
<220> FEATURE:
<223> OTHER INFORMATION: Synthetic Construct

<400> SEQUENCE: 16

Gly Gly Gly Glu Ile Ala Ala Ile Lys Lys Glu Ile Ala Ala Ile Lys
1               5                   10                  15

Cys Glu Ile Ala Ala Ile Lys Gln Gly Tyr Gly
            20                  25

<210> SEQ ID NO 17
<211> LENGTH: 47
<212> TYPE: PRT
<213> ORGANISM: Artificial Sequence
<220> FEATURE:
<223> OTHER INFORMATION: Synthetic Construct

<400> SEQUENCE: 17

Ile Asp Lys Ile Ser Asp Val Ser Thr Ile Val Pro Tyr Ile Gly Pro
1               5                   10                  15

Ala Leu Asn Ile Gly Gly Gly Lys Ile Ala Ala Leu Lys Lys Lys Asn
            20                  25                  30

Ala Ala Leu Lys Cys Lys Ile Ala Ala Leu Lys Gln Gly Tyr Trp
        35                  40                  45

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

```
Lys Lys Lys Lys
1

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Lys Lys Lys Lys Gly Gly
1               5

<210> SEQ ID NO 20
<211> LENGTH: 20
<212> TYPE: PRT
<213> ORGANISM: Artificial Sequence
<220> FEATURE:
<223> OTHER INFORMATION: Synthetic Construct

<400> SEQUENCE: 20

Ile Asp Lys Ile Ser Asp Val Ser Thr Ile Val Pro Tyr Ile Gly Pro
1               5                   10                  15

Ala Leu Asn Ile
            20

<210> SEQ ID NO 21
<211> LENGTH: 25
<212> TYPE: PRT
<213> ORGANISM: Artificial Sequence
<220> FEATURE:
<223> OTHER INFORMATION: Synthetic Construct

<400> SEQUENCE: 21

Gly Glu Ile Ala Ala Leu Glu Lys Glu Asn Ala Ala Leu Glu Gln Glu
1               5                   10                  15

Ile Ala Ala Leu Glu Gln Gly Trp Trp
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthetic Construct

<400> SEQUENCE: 22

Gly Lys Ile Ala Ala Leu Lys Lys Lys Asn Ala Ala Leu Lys Gln Lys
1               5                   10                  15

Ile Ala Ala Leu Lys Gln Gly Tyr Trp
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23
```

```
Gly Glu Ile Ala Ala Ile Lys Lys Glu Ile Ala Ala Ile Lys Gln Glu
1               5                   10                  15
Ile Ala Ala Ile Lys Gln Gly Tyr Gly
                20              25
```

US 9,562,074 B2

SELF-ASSEMBLING PEPTIDE CAGES FROM COILED-COIL PEPTIDE MODULES

FIELD OF THE INVENTION

This invention relates to protein structures, to methods of producing those protein structures, and to peptides used in the formation of the protein structures.

BACKGROUND

As our understanding of sequence-to-structure relationships in proteins improves, so does our ability to rationally design new proteins and protein-based materials. Unlike discrete peptide and protein objects, the design of biomaterials requires additional rules for self-assembly to allow the nano-to-micron scale regimes to be bridged (Woolfson, D. N. & Ryadnov, M. G. *Curr. Opin. Chem. Biol.* 10, 559-567 (2006); Ulijn, R. V. & Smith, A. M. *Chem. Soc. Rev.* 37, 664-675 (2008)). In these respects, synthetically accessible peptides, which can be programmed to fold into prescribed structures and to self-assemble into larger architectures, offer routes to rationally designed peptide and protein-based biomaterials. Indeed, a variety of peptide-based self-assembling fibres, tapes and hydrogels have been produced (Zhang, S. G., Holmes, T., Lockshin, C. & Rich, A. *Proc. Natl. Acad. Sci. USA* 90, 3334-3338 (1993); Aggeli, A. et al., *Nature* 386, 259-262 (1997); Pandya, M. J. et al., *Biochemistry* 39, 8728-8734 (2000); Hartgerink, J. D., Beniash, E. & Stupp, S. I. *Science* 294, 1684-1688 (2001); Schneider, J. P. et al., *J. Am. Chem. Soc.* 124, 15030-15037 (2002); Paramonov, S., Gauba, V. & Hartgerink, J. *Macromolecules* 38, 7555-7561 (2005)). Much of this effort has been directed to the assembly of β-structured systems, though α-helix-based fibrous and α-helix-containing gelling materials have been explored to some extent (Pandya et al., 2000 supra; Petka, W. A., Harden, J. L., McGrath, K. P., Wirtz, D. & Tirrell, D. A. *Science* 281, 389-392 (1998); Wang, C., Stewart, R. J. & Kopecek, J. *Nature* 397, 417-420 (1999); Potekhin, S. A. et al., *Chem. Biol.* 8, 1025-32 (2001); Zimenkov, Y., Conticello, V. P., Guo, L. & Thiyagarajan, P. *Tetrahedron* 60, 7237-7246 (2004); Dong, H., Paramonov, S. E. & Hartgerink, J. D. *J. Am. Chem. Soc.* 130, 13691-13695 (2008); Gribbon, C. et al., *Biochemistry* 47, 10365-10371 (2008)).

In WO 2001/021646, the inventors described a self-assembling fibre (SAF) system enabling the sticky-end directed molecular assembly of α-helical coiled coils. The system comprises two short peptides (SAF-p1 and SAF-p2) of de novo design. The SAF-p1 and SAF-p2 sequences were designed to co-assemble, resulting in an offset α-helical dimer with complementary sticky ends. The ends promote longitudinal assembly into α-helical coiled-coil fibrils, which bundle to form matured fibres. Subsequently, the inventors introduced fibre-shaping peptides into the SAF system allowing morphological changes to be made to protein fibres comprising self-assembling peptides (WO 2004/022584).

In viruses (H. F. Lodish, *Molecular cell biology*. (W.H. Freeman, New York, ed. 6th, 2008)) and certain bacterial microcompartments (S. Tanaka et al., *Science* 319, 1083 (2008)), capsids and suprastructures are produced via the self-assembly of large folded proteins, usually in highly symmetric manners, and with exquisite positioning of non-covalent protein-protein interactions. Biomimetic assemblies have potential for creating simpler encapsulation systems, and for applications in controlled delivery and release, sensing, and the preparation of protocells for various aspects of synthetic biology (C. M. Agapakis, P. M. Boyle, P. A. Silver, *Nat. Chem. Biol.* 8, 527 (2012); D. A. Hammer, N. P. Kamat, *FEBS Lett.* 586, 2882 (2012); M. Uchida et al., *Adv. Mater.* 19, 1025 (2007)). To these ends, others have produced macroscopic "sacs" from peptide amphiphiles (R. M. Capito, H. S. Azevedo, Y. S. Velichko, A. Mata, S. I. Stupp, *Science* 319, 1812 (2008)); and engineered micelle-like structures (F. Boato et al., *Angew. Chem. Int. Ed. Engl.* 46, 9015 (2007); S. Raman, G. Machaidze, A. Lustig, U. Aebi, P. Burkhard, *Nanomedicine* 2, 95 (2006)), small polyhedra (N. P. King et al., *Science* 336, 1171 (2012); Y. T. Lai, D. Cascio, T. 0. Yeates, *Science* 336, 1129 (2012)), extended protein arrays (J. C. Sinclair, K. M. Davies, C. Venien-Bryan, M. E. M. Noble, *Nat. Nanotechnol.* 6, 558 (2011)), and metal-directed assemblies (J. D. Brodin et al., *Nat. Chem.* 4, 375 (2012); M. M. Pires, J. Lee, D. Ernenwein, J. Chmielewski, *Langmuir* 28, 1993 (2012)) using mainly natural peptides and proteins.

The inventors have produced self-assembled cage-like particles, SAGEs, from a set of short, de novo, α-helical, coiled-coil peptides by employing clear sequence-to-structure relationships and rational-design principles to direct stable and highly specific protein-protein interactions. Such sequence-to-structure relationships and rational-design principles are described in E. H. C. Bromley, K. Channon, E. Moutevelis, D. N. Woolfson, *ACS Chem. Biol.* 3, 38 (2008); A. N. Lupas, M. Gruber, *Adv. Prot. Chem.* 70, 37 (2005); and D. N. Woolfson, *Adv. Prot. Chem.* 70, 79 (2005).

SUMMARY OF THE INVENTION

According to the first aspect of the invention there is provided a self-assembled cage-like (SAGE) particle comprising a plurality of first hubs and a plurality of second hubs, wherein:
  i. each of the first hubs comprises a core comprising a trimeric, tetrameric or hexameric coiled coil peptide structure, wherein the core of the first hub is linked to at least 3 first peptides, wherein each first peptide is capable of interacting with a second peptide to form a dimeric coiled coil structure; and
  ii. each of the second hubs comprises a core comprising a trimeric, tetrameric or hexameric coiled coil peptide structure, wherein the core of the second hub is linked to at least 3 second peptides, wherein each second peptide is capable of interacting with the first peptide to form a dimeric coiled coil structure,
wherein the first hubs and the second hubs interact by the formation of dimeric coiled core structures between the first and second peptides.

The self-assembled cage-like particle of the present invention is a particle formed from a number of peptides that interact to form a network which closes to form a sphere. The self-assembled cage-like particle has a hollow core and surface pores of around 2 to 10 nm. The size of the particle can vary depending on the specific structure of the peptides used to form the particle as is discussed in further detail herein. Generally the self-assembled cage-like particle has a diameter ranging from about 50 nm to 150 nm.

The SAGE particles (also referred to herein as cages) have a simple structure and are assembled from modular components (i.e., peptides). Accordingly, there is enormous scope to tailor them for specific applications. Indeed, objects could be encapsulated on the inside (either passively or actively), or presented on the exterior surface of the particle, or both. Further, given the number of individual peptides that make up a single particle (generally around 10,000 individual peptide chains) multiple molecules can be presented simultaneously on the exterior surface of the particles. The number of molcules presented (or encapsulated) in this way can be varied by changing the ratio of normal and "decorated" hubs.

With an ability to encapsulate objects within and/or present molecules on the surface of these cage-like assemblies, the SAGE particles have a variety of applications. Certain applications are discussed in further detail herein.

The cage is hollow, allowing a variety of objects (from proteins, and other biologicals to artificial nanoscale objects such as quantum dots, etc.) to be encapsulated. This may be done in either a passive fashion (simply forming the cages in the presence of the object to be encapsulated) or an active one (exploiting bespoke ligand binding pairs, such as biotin & streptavidin or safety-catch (Zakeri et al., Proc Natl Acad Sci U S A 109(12):E690-7) systems).

The cage is semi-permeable due to the presence of pores. This allows for larger objects (such as proteins) to be encapsulated whilst smaller substrates and other smaller molecules are free to diffuse in and out.

The design of SAGE particles according to the invention is modular and flexible. There is control over the size of the cages and scope to make a variety of modifications to the system, thus tailoring its properties for a given application.

The core structures comprise trimeric, tetrameric or hexameric coiled coil peptide structures. Such structures are well known to those skilled in the art (see, for example, Fletcher et al., ACS Synth. Biol., 1, 240-250, 2012; Nautiyal et al., Biochemisty, U34U, 11645-11651, 1995; and Zaccai et al., Nature Chemical Biology, 7, 935-941, 2011). Preferably the core structure is a trimeric coiled coil peptide structure or a tetrameric coiled coil peptide structure. Most preferably, the core structure is a trimeric coiled coil peptide structure. The core structure can be a homomeric coiled coil peptide structure or heteromeric coiled coil peptide structure. Preferably the core structure is a homotrimeric coiled coil peptide structure or a homotetrameric coiled coil peptide structure. Most preferably, the core structure is a homotrimeric coiled coil peptide structure.

The first peptide and the second peptide can be linked to the trimeric, tetrameric or hexameric coiled coil peptide structure (i.e., the core structure) via any suitable linkage, including covalent and non-covalent linkages. Preferably the first and second peptides are linked to the core structure via covalent linkages, most preferably disulfide linkages. The first and second peptides can be linked to the core via a flexible peptide linker resulting in the formation of single chain helix turn helix peptides.

The first and second peptides together form a dimeric coiled coil peptide structure. Such structures are well known to those skilled in the art (see, for Example, Fletcher et al., ACS Synth. Biol., 1, 240-250, 2012; and Thomas et al., J. Am. Chem. Soc., 2013, 135 (13), pp 5161-5166). The dimeric coiled coil structure can be a homomeric coiled coil peptide structure or heteromeric coiled coil peptide structure. Preferably the dimeric coiled coil structure is a heterodimeric coiled coil peptide structure.

As will be appreciated by those skilled in the art the multimeric coiled coil peptide structures may be a parallel or antiparallel structure. Preferably the multimeric coiled coil structures are parallel structures.

When the core structure is a trimeric structure, preferably 3 of the first peptides or the second peptides are linked to the core. In particular, preferably each of the 3 peptides making up the trimeric core structure is linked to one of the first peptides or the second peptides, i.e., one of the first peptides or the second peptides is linked to each of the three peptides making up the trimeric core. An example of such a structure is shown schematically in FIG. 1.

When the core structure is a homomeric coiled coil structure, preferably the first and second peptides form a heterodimeric coiled coil peptide structure. When the core structure is a heteromeric coiled coil structure, preferably the first and second peptides form a homodimeric coiled coil peptide structure.

When the core structure is a tetrameric structure, preferably 4 of the first peptides or the second peptides are linked to the core. In particular, preferably each of the 4 peptides making up the tetrameric core structure is linked to one of the first peptides or the second peptides, i.e., one of the first peptides or the second peptides is linked to each of the four peptides making up the tetrameric core. An example of such a structure is shown schematically in FIG. 4.

When the core structure is a hexameric structure, preferably 3 of the first peptides or the second peptides are linked to the core. In particular, preferably 3 of the 6 peptides making up the hexameric core structure are linked to one of the first peptides or the second peptides, i.e., one of the first peptides or the second peptides is linked to 3 of the 6 peptides making up the hexameric core. An example of such a structure is shown schematically in FIG. 6.

Each peptide making up the dimeric, trimeric, tetrameric and hexameric coiled coil peptide structures is a peptide forming a coiled coil structure. The term "coiled coil" refers to a peptide/protein sequence usually with a contiguous pattern of hydrophobic residues spaced 3 and 4 residues apart, which assembles (folds) to form a multimeric bundle of helices. Preferably, the peptides making up the multimeric structures form purely α-helical coiled-coils. The peptides can be any suitable size, for example between about 21 and 42 amino acids.

The peptides making up the multimeric structures comprise a repeating structural unit. Preferably, the repeating structural unit comprises a heptad repeat motif (abcdefg). Other repeats (e.g hendecads—abcdefghijk) and amino acid compositions may also be used (see WO99/11774).

Those skilled in the art understand how to design the necessary peptides to make up the required multimeric structures (see e.g., Fletcher et al., 2012 supra). For example, a coiled coil typically possesses a heptad repeat (gabcdef) where a and d residues are hydrophobic and the remainder more polar. Preferably, when forming a trimeric coiled coil structure there should be an all isoleucine core, i.e., isoleucine residue are at positions a and d in each gabcdef hepad of the three peptides used to form the trimeric structure. However, addition variants can have asparagine at d. The peptides used to form the trimeric structure should posses oppositely charged residues at g and e positions in each gabcdef heptad. Such as glutamic acid at g and lysine at e, or, alternatively, glutamic acid at e and lysine at g. Other charge patterns are possible and may be different for each heptad. In this way for example it is possible to make a heterotrimeric structure (Nautiyal, S., D. N. Woolfson, D. S. King and T. Alber (1995). "A designed heterotrimeric coiled coil." *Biochemistry* 34: 11645-11651). When forming a heterodimeric coiled coil structure, each peptide should posses isoleucine residues at a and leucine residues at d in each gabcdef heptad repeat. A single asparagine residue at an a position can also be incorporated to specify dimeric oligomeric state, parallel assembly and effect stability. The heterodimer is produced from two different peptides which are largely unfolded alone, but form a heterodimeric coiled coil when mixed. The two peptides comprising the heterodimeric coiled coil should posses complementarily charged residues at g and e positions to maximise heterotypic assembly and minimise homotypic assembly. To assist all the peptides with forming the coiled coil structure residues at b and c in each heptad repeat should be helix favouring (e.g., Alanine).

The peptides used to form the coiled coils modules should be between 3 and 6 heptads in length.

The peptides may possess a chromophore (such as Tyrosine or Tryptophan) as this helps with determining the concentration of the peptides in a sample. Such a chromophore may be at positon f in a heptad.

As the core structure is linked to either the first peptide or the second peptide that together form the dimeric coiled coil structure, residues must be provided to enable such a link to be formed. For example, one residue on each of the peptides forming the core structure, and each of the first and second peptides should provide a suitable chemically addressable functionality allowing a covalent bond to be formed. One option is to place a cysteine residue at f in one of the heptad repeats of each of the peptides making up the core structure and in the first and second peptides, between which a disulfide bond may be formed. When the core structure is a hexameric structure not all of the 6 peptides making up the core structure need to be linked to the first or second peptides. Instead, and as indicated above, only 3 of the 6 peptides making up the hexameric core structure need to be designed so that they can be linked to the first or second peptides.

It is also noted that the size of SAGE particles can be controlled by altering the affinity between the first and second peptides that interact to form the dimeric coiled coil structure. The stronger the affinity the smaller the SAGE particles. The size of SAGE particles can also be controlled by altering residues present at f positions. For example, by placing a glutamine residue instead of a lysine residue at f position of the first heptad in the each of the peptides reduces curvature and thereby increases the size of the SAGE particle.

The term "amino acid" embraces both naturally occurring amino acids, synthetic amino acids and naturally occurring amino acids that have been modified. In all cases references to naturally occurring amino acids may be considered to include synthetic amino acids which may be substituted therefor.

According to one aspect of the present invention, the core structure is a homotrimeric coiled coil structure, wherein each peptide of the trimeric coiled coil structure has the following sequence:

(SEQ ID NO. 1)
G EIAAIKK EIAAIKC EIAAIKQ GYG

According to a further aspect of the present invention the core structure is a homotrimeric coiled coil structure, wherein each peptide of the trimeric coiled coil structure has the following sequence:

(SEQ ID NO. 15)
KKKKGGG EIAAIKK EIAAIKC EIAAIKQ GYG

According to a further aspect of the present invention the core structure is a homotrimeric coiled coil structure, wherein each peptide of the trimeric coiled coil structure has the following sequence:

(SEQ ID NO. 16)
(5(6)-Carboxyfluorescein)-GGG EIAAIKK EIAAIKC EIAAIKQ GYG

According to a further aspect of the present invention, the core structure is a homotetrameric coiled coil structure, wherein each peptide of the tetrameric coiled coil structure has the following sequence:

(SEQ ID NO. 2)
G ELAAIKQ ELAAIKK ELAAIKC ELAAIKQ GAG

Accordingly to a further aspect of the present invention, the first peptide and the second peptide together form a heterodimeric coiled coil structure and have the following sequences, respectively:

(SEQ ID NO. 3)
G EIAALEK ENAALEC EIAALEQ GWW (SEQ ID NO. 4)
G KIAALKK KNAALKC KIAALKQ GYW.

Accordingly to a further aspect of the present invention, the first peptide and the second peptide together form a heterodimeric coiled coil structure and have the following sequences, respectively:

(SEQ ID NO. 3)
G EIAALEK ENAALEC EIAALEQ GWW (SEQ ID NO. 17)
IDKIS DVSTI VPYIG PALNI GGG KIAALKK KNAALKC KIAALKQ GYW.

Alternatively, the first peptide and the second peptide together form a heterodimeric coiled coil structure and have the following sequences, respectively:

(SEQ ID NO. 5)
G EIAALEK EIAALEC EIAALEQ GWW (SEQ ID NO. 6)
G KIAALKK KIAALKC KIAALKQ GYW.

In SEQ ID NO. 5 and 6 isoleucine is present at position a in the second heptad repeat. The presence of this amino acid causes the size of the SAGE particle to be smaller.

The core structure formed from peptides having the sequence given in SEQ ID NO. 1, 2, 15 or 16 is preferably used with the first and second peptides having the sequences given in SEQ ID NO. 3 and 4, respectively, in order to form the first and second hubs and the SAGE particles of the present invention. Alternatively, the core structure formed from the peptides having the sequence given in SEQ ID NO. 1, 2, 15 or 16 is used with the first and second peptides having the sequences given in SEQ ID NO. 5 and 6, respectively, in order to form the first and second hubs and the SAGE particles of the present invention. Alternatively, the core structure formed from the peptides having the sequence given in SEQ ID NO. 1, 2, 15 or 16 is used with the first and second peptides having the sequences given in SEQ ID NO. 3 and 17, respectively, in order to form the first and second hubs and the SAGE particles of the present invention.

Alternatively, the core structure is a homotrimeric coiled coil structure, wherein each peptide of the trimeric coiled coil structure has the following sequence:

```
                                              (SEQ ID NO. 7)
G EIAAIKQ EIAAIKC EIAAIKQ GYG.
```

When the homotrimeric coiled coil structure has SEQ ID NO. 7, i.e., wherein glutamine is present at position f in the first heptad, it is preferred that the first peptide and the second peptide, which together form a heterodimeric coiled coil structure, have the following sequences, respectively:

```
                                              (SEQ ID NO. 8)
G EIAALEQ ENAALEC EIAALEQ GWW (SEQ ID NO. 9)
G KIAALKQ KNAALKC KIAALKQ GYW.
```

In SEQ ID NO. 8 and 9 glutamine is present at position f in the first heptad. The presence of gluatamine at this position within the peptide sequences results in a larger SAGE particle.

According to a further aspect of the present invention, the core structure is a hexameric coiled coil structure, wherein three of the peptides forming the structure have the sequence:

```
                                             (SEQ ID NO. 10)
GELKAIAQELKAIAKELKAIAWEDKAIAQGAGY
``` and the other three peptides have the sequence:

```
                                             (SEQ ID NO. 11)
GELKAIAQELKAIAKELKAIAWEHKAIAQGAG.
```

The hexameric core structure comprising peptides having SEQ ID NO. 10 and 11 is preferably used with the first and second peptides of a homodimer, such as those described in Fletcher et al., 2012 supra, in order to form the first and second hubs and the SAGE particles of the present invention.

According to one aspect of the present invention, the core structure is a heterotrimeric coiled coil structure, wherein the peptides of the trimeric coiled coil structure have the following sequences:

```
                                             (SEQ ID NO. 12)
G EIAAIEQ EIAANKK EIAAIKW KIAAIKQ G (SEQ ID NO. 13)
G KIAAIKQ EIAANEK EIAAIKW EIAAIKQ G (SEQ ID NO. 14)
G EIAAIKQ KIAANKK EIAAIKW EIAAIEQ G
```

The heterotrimeric core structure comprising peptides having SEQ ID NO. 12 to 14 is preferably used with the first and second peptides of a homodimer, such as those described in Fletcher et al., 2012 supra, in order to form the first and second hubs and the SAGE particles of the present invention.

Other functionally equivalent peptide sequences having at least 85%, preferably 90%, and most preferably at least 95% sequence identity to the sequences indicated above (SEQ ID NO. 1 to 17) may also be used to form the SAGE particles of the present invention. The term functionally equivalent peptide sequences as used herein means that the peptides still funtion to form the multimeric structures, the hubs and the SAGE particles.

One or more amino acid residues (e.g., one, two or three amino acid residues) may be substituted with an amino acid that has been derviatised (e.g., derivatised with a functional group that is compatible with click chemistry). Substitution may occur at any position and by any derivatised amino acid provided that the peptides are still able to interact to form the SAGE particles. It is also possible to address the termini of the peptides as well as the side chains. In particular, the N-termini as this appears to be facing the "outside" of the particles. Preferably, the amino acid residue alanine or glutamine is substituted. More preferably, alanine is substituted. The amino acid residues are preferably substituted by a derivatised lysine residue. In addition, substitution can occur at any position in the peptide. Substitution can occur near or at the N-terminus or the C-terminus of the peptide. For encapsulating bioactive molecules within the SAGE particles, preferably, substitution occurs near or at the C-terminus of the heptad (i.e., the f position). More preferably, substitution occurs near or at the C-terminus of the most C-terminal heptad. For presenting bioactive molecules on the outside of the SAGE particles, preferably, substitution occurs near or at the N-terminus of the heptad (i.e., the f position). More preferably, substitution occurs near or at the N-terminus of the most C-terminal heptad.

Methods for derivatising peptides are well known to those skilled in the art. The peptides may be derivatised through non-covalent or covalent binding. Derivatisation through non-covalent binding can be achieved, for example, using hydrophobic interactions, electrostatic interactions (such as negatively charged peptides (e.g. DE-based peptides), and neutral peptides (e.g. AQ-based peptides)), structural mimics and complementary pairing (Mahmoud, Z. N., S. B. Gunnoo, A. R. Thomson, J. M. Fletcher and D. N. Woolfson (2011) Biomaterials 32: 3712-3720; Woolfson, D. N. and Z. N. Mahmoud (2010) Chem Soc Rev 39: 3464-3479; Mahmoud, Z. N., D. J. Grundy, K. J. Channon and D. N. Woolfson (2010) Biomaterials 31: 7468-7474). Derivatisation through covalent binding can be achieved through, for example using recombinant expression, hybrid systems or click chemistry (Woolfson and Mahmound, 2010). In a preferred embodiment of the present invention, derivatisation is achieved using click chemistry, as described in Woolfson and Mahmound, 2010.

"Click chemistry" (also known as "click reactions") is a term well-known to those skilled in the art. It refers to the concept of generating substances by joining small modular units together. Exemplary click reactions include, but are not limited to, Huisgen 1,3-dipolar cycloaddition (e.g. the copper(I)-catalyzed azide-alkyne cycloaddition), the Diels-Alder reaction, nucleophilic substitution (such as to small strained rings like epoxy and aziridine compounds), oxime ligation, hydrazone ligation, thiazolidine ligation, dihydroxylation (for addition to C=C) and thiol-yne reaction (for addition to alkynes). In particular, the peptides of the present invention may be derivatised so that they contain a first click group. The derivatised peptides can then be functionalised through conjugation with moieties/macromolecules having a complementary second click group using, for example copper-catalysed azide-alkyne or thiolene click reactions.

In addition, bioactive peptides and proteins could simply be added to the N- or C-termini of the hub component peptides either through standard peptide synthesis or recombinant expression of synthetic genes in bacteria, yeast and other suitable hosts.

In one embodiment, a molecule may be added to at least one of the peptides forming the first and/or second hubs. Preferably the molecule is added to at least one of the peptides forming the core of the first and/or second hubs. The molecule may be added at any point on the peptide using any of the techniques described above or, when the functional element is an amino acid or peptide, synthesised as part of the peptide. Preferably the molecule is added to the N-terminus and/or the C-terminus of at least one of the peptides forming the first and/or second hubs. Preferably, the molecule is added to the N-terminus of the peptide so that it is displayed on the surface of the SAGE particle. The molecule may be any suitable molecule including cationic elements, labels, antigenic peptides, chemically addressable functionalities for subsequently attaching other molecules, targeting moieties for targeting the SAGE particles to cell receptors, enzymes, therapeutic proteins, adjuvants and pharmaceutical agents. It has been found that the presence of such a molecule on at least one of the peptides forming the first and/or second hubs does not interfere with the formation of the SAGE particles or affect the stability of the SAGE particles.

The molecule can be directly connected to at least one of the peptides forming the first and/or second hubs. Alternatively, molecule can be connected to at least one of the peptides forming the first and/or second hubs via a linker sequence. Any suitable linker sequence may be used and suitable linker sequences are well known to those skilled in the art. The linker sequence may comprise from 1 to 6 amino acids and is preferably formed from Glycine residues. Most preferably the linker is Gly-Gly.

In one embodiment, the molecule is a cationic element. Preferably, the cationic element is added to the N-terminus of the peptide. The cationic element may be any cationic element but is preferably a cationic amino acid or cationic peptide sequence. Suitable cationic amino acids that can be used include Lysine and Arginine. Preferably the cationic element comprises from 1 to 10, more preferably from 1 to 6, and most preferably around 4 cationic amino acids. Preferably the cationic amino acids are Lysine, and preferably the cationic element comprises tetralysine (Lys-Lys-Lys-Lys (SEQ ID NO. 18)). In a particularly preferred embodiment, the cationic element has the sequence Lys-Lys-Lys-Lys (SEQ ID NO. 18) and is preferably linked to the N-terminus of at least one of the peptides forming the first and/or second hubs via a -Gly-Gly- linker. It has been found that the use of a cationic element on the end of at least one of the peptides forming the first and/or second hubs reduces the level of clumping of the SAGE particles. The presence of the cationic element does not interfere with the formation of the SAGE particles or affect the stability of the SAGE particles.

In a further embodiment, the molecule is a label. The label may be added at any point on the peptide using any of the techniques described above. Preferably the label is added to the N-terminus and/or the C-terminus of the peptide. The label is preferably connected to the peptide via a linker as described above. The label may be any suitable label such as carboxyfluorescein or any other fluorophore. The use of such labels enables the easy identification of the particles. The presence of the label does not interfere with the formation of the SAGE particles or affect the stability of the SAGE particles.

In a further embodiment, the molecule is an antigenic peptide. Preferably the antigenic peptide is added to the N-terminus of the peptide so that it is presented on the surface of the SAGE particles. The antigenic peptide is preferably connected to the peptide via a linker as described above. The antigenic peptide may be any suitable antigenic peptide. In the examples below, the antigenic peptide is the tetanus toxoid peptide 632-651. This peptide is used to demonstrate the principle. One skilled in the art will appreciate that any suitable antigenic peptide can be used. The use of an antigenic peptide means that the SAGE displaying the antigenic peptide can be used to raise an immune response. The presence of the antigenic peptide does not interfere with the formation of the SAGE particles or affect the stability of the SAGE particles.

According to another aspect of the invention, there is provided a method of producing a self-assembling cage-like particle of the present invention, the method comprising providing a plurality of first hubs and a plurality of second hubs, wherein:
  i. each of the first hubs comprises a core comprising a trimeric, tetrameric or hexameric coiled coil peptide structure, wherein the core of the first hub is linked to at least 3 first peptides, wherein each first peptide is capable of interacting with a second peptide to form a dimeric coiled coil structure; and
  ii. each of the second hubs comprises a core comprising a trimeric, tetrameric or hexameric coiled coil peptide structure, wherein the core of the second hub is linked to at least 3 second peptides, wherein each second peptide is capable of interacting with the first peptide to form a dimeric coiled coil structure,
  and mixing said first and second hubs together.

The first and second hubs have the characteristics described above.

According to yet another aspect of the invention, there is provided a kit for making a self-assembling cage-like particle, the kit comprising a plurality of the first hubs and a plurality of the second hubs, wherein
  i. each of the first hubs comprises a core comprising a trimeric, tetrameric or hexameric coiled coil peptide structure, wherein the core of the first hub is linked to at least 3 first peptides, wherein each first peptide is capable of interacting with a second peptide to form a dimeric coiled coil structure; and
  ii. each of the second hubs comprises a core comprising a trimeric, tetrameric or hexameric coiled coil peptide structure, wherein the core of the second hub is linked to at least 3 second peptides, wherein each second peptide is capable of interacting with the first peptide to form a dimeric coiled coil structure,
  wherein upon mixing the first and second hubs associate to form the SAGE particle.

The SAGE particles of the present invention can be used to encapsulate any molecule. Preferably the molecule is larger than the pores of the SAGE particles, e.g., greater than 10 nm, so that it is retained within the particle. Suitable molecules include proteins, especially enzymes, viruses, DNA or RNA molecules, etc. Encapsulation can be performed in a passive fashion, i.e., simply by forming the SAGE particles in the presence of the molecule of interest, or actively by exploiting specific binding pairs to link the molecule to peptides forming the particle. Suitable binding pairs include biotin/streptavidin and safety catch (Zakeri et al., PNAS USA 109 (12), E690-7) systems.

The SAGE particles can be used to delivery molecules to cells in culture or in vivo. When the linkage between the core structure and the first or second peptide is a disulfide linkage, the reducing nature of the intracellular environment has the effect of reducing the disulfide bond and rupturing the SAGE particle, and thereby releasing any encapsulated molecules.

As indicated above, the SAGE particles can be produced with molecules presented on the surface of the particles. Methods for attaching molecules to the peptides so that they are presented on the surface of the molecule will be apparent to those skilled in the art. For example, molecules can be presented on the surface by extending the linear sequence of the peptide(s) with the sequence (or molecule) of interest. Furthermore, molecules can also be added to the surface of SAGE particles Post-Assembly. Incorporating a chemically addressable functionality to the termini of the coiled coil peptides will enable chemistry to be performed on the assembled SAGE molecule which may then be functionalised with the molecule(s) of interest (see the discussion above). Molecules that can be presented on the surface of the SAGE particles include molecules that target the particles to specific cell types (e.g., peptide motifs and antibody molecules, having affinity for specific cell receptors), antigenic peptides and proteins, adjuvants, a label (e.g., a fluorescent tag), etc.

As indicated above, the SAGE particles of the present invention can be used for vaccine delivery/presentation. As a proteinaceous, hexagonally-arranged, nanoscale sphere, the SAGE particle of the present invention shares several salient features with viral capsids. Given the modularity of the system, there is the capacity to modify the surface of the cages or to present molecules at the surface of the cage. These properties make it an ideal choice for vaccine delivery and presentation of antigenic peptides. Indeed, an array of antigenic peptides could be presented simultaneously, alongside other molecules, including, but not limited to, fluorescent molecules for tracking, or peptide adjuvants. Further, unlike most vaccines currently on the market, the current invention does not require an unbroken cold chain. This raises tremendous potential in that the components for assembling the SAGE particles upon which the antigenic peptides are presented could be simply mailed to the customer/patient, water added allowing the cages to self-assemble, and the sample injected. This would be particularly advantageous in the developing world.

The SAGE particles can also be used for intracellular delivery and targeting. Being hollow, objects can be encapsulated. Because the system is two component, there is temporal control over the assembly of the cages. Thus, a protein of interest may be encapsulated inside the cages by simply being present in solution when the two components are mixed. Secondly, the skilled addressee may modify the modular components from which the cages are assembled, effectively presenting molecules on the surface of the assembled cages. This enables the skilled addressee to target specific cell types and exploit various modes of cellular uptake. Further, and as indicated above, as the peptides forming the particles can be linked together by a disulfide bond which will be reduced intracellularly resulting in the release of any encapsulated molecule.

The SAGE particles can also be used as compartments for biological factories. A unique feature of the SAGE particle of the present invention is that whilst it is a device which may be used to encapsulate objects, it is also permeable to small molecules due to the presence of the pores. This effectively means that objects the size of medium to large proteins (or larger) (i.e., greater than about 10 nm) can be trapped inside, whilst smaller peptide and organic molecules are free to diffuse in and out. As such, the SAGE particles can be used as a device for encapsulating biological machinery (such as enzymes) whilst substrates, products, co-factors and other small molecules are free to diffuse in and out.

The present invention also provides a peptide having one of the following sequences:

```
                                        (SEQ ID NO. 1)
   G EIAAIKK EIAAIKC EIAAIKQ GYG;

(SEQ ID NO. 2)
   G ELAAIKQ ELAAIKK ELAAIKC ELAAIKQ GAG;

(SEQ ID NO. 3)
   G EIAALEK ENAALEC EIAALEQ GWW;

(SEQ ID NO. 4)
   G KIAALKK KNAALKC KIAALKQ GYW;

(SEQ ID NO. 5)
   G EIAALEK EIAALEC EIAALEQ GWW;

(SEQ ID NO. 6)
   G KIAALKK KIAALKC KIAALKQ GYW;

(SEQ ID NO. 7)
   G EIAAIKQ EIAAIKC EIAAIKQ GYG;

(SEQ ID NO. 8)
   G EIAALEQ ENAALEC EIAALEQ GWW;

(SEQ ID NO. 9)
   G KIAALKQ KNAALKC KIAALKQ GYW;

(SEQ ID NO. 12)
   G EIAAIEQ EIAANKK EIAAIKW KIAAIKQ G;

(SEQ ID NO. 13)
   G KIAAIKQ EIAANEK EIAAIKW EIAAIKQ G;
   and (SEQ ID NO. 14)
   G EIAAIKQ KIAANKK EIAAIKW EIAAIEQ G.
```

The present invention also provides a peptide having the sequence selected from the sequences indicated above as SEQ ID NO. 1 to 9 and 12 to 14, wherein a molecule as defined above is attached directly or via a linker sequence to the N-terminus or C-terminus of the peptide.

The present invention further provides a peptide having one of the following sequences:

```
                                       (SEQ ID NO. 15)
KKKKGGG EIAAIKK EIAAIKC EIAAIKQ GYG (SEQ ID NO. 16)
(5(6)-Carboxyfluorescein)-GGG EIAAIKK EIAAIKC

EIAAIKQ GYG (SEQ ID NO. 17)
IDKIS DVSTI VPYIG PALNI GGG KIAALKK KNAALKC KIAALKQ

GYW
```

The present invention also provides a functionally equivalent peptide having at least 85%, preferably 90%, and most preferably at least 95% sequence identity to any one of SEQ ID NO. 1 to 9 and 12 to 17. As indicated above, the functionally equivalent peptide must still function, in combination with the other relevant peptides, to form the multimeric structure, the hubs and the SAGE particles of the present invention. As will be appreciated by those skilled in the art the cysteine residue in SEQ ID NO. 1 to 9 and 12 to 17 must be maintained in order to allow the linkage to be formed between the peptides of the core structure and the first and second peptides.

The present invention also provides a hub comprising the peptide having SEQ ID NO.1 linked to any one of peptides having SEQ ID NO. 3 to 6 via a disulfide linkage between the cysteine residues.

The present invention also provides a hub comprising the peptide having SEQ ID NO.2 linked to any one of peptides having SEQ ID NO. 3 to 6 via a disulfide linkage between the cysteine residues.

The present invention also provides a hub comprising the peptide having SEQ ID NO.7 linked to any one of peptides having SEQ ID NO. 8 to 9 via a disulfide linkage between the cysteine residues.

The present invention also provides a hub comprising the peptide having SEQ ID NO. 15 linked to any one of peptides having SEQ ID NO. 3 to 6 via a disulfide linkage between the cysteine residues.

The present invention also provides a hub comprising the peptide having SEQ ID NO. 16 linked to any one of peptides having SEQ ID NO. 3 to 6 via a disulfide linkage between the cysteine residues.

The present invention also provides a hub comprising the peptide having SEQ ID NO. 1, 2, 15 or 16 linked to a peptide having SEQ ID NO. 17 via a disulfide linkage between the cysteine residues.

As will be appreciated by those skilled in the art functionally equivalent peptides having at least 85%, preferably 90%, and most preferably at least 95% sequence identity to any one of SEQ ID NO. 1 to 9 and 15 to 17, can be used in place of SEQ ID NO. 1 to 9 and 15 to 17 in order to form a hub according to the present invention.

MATERIALS AND METHODS

Peptide Synthesis

Figure 1:
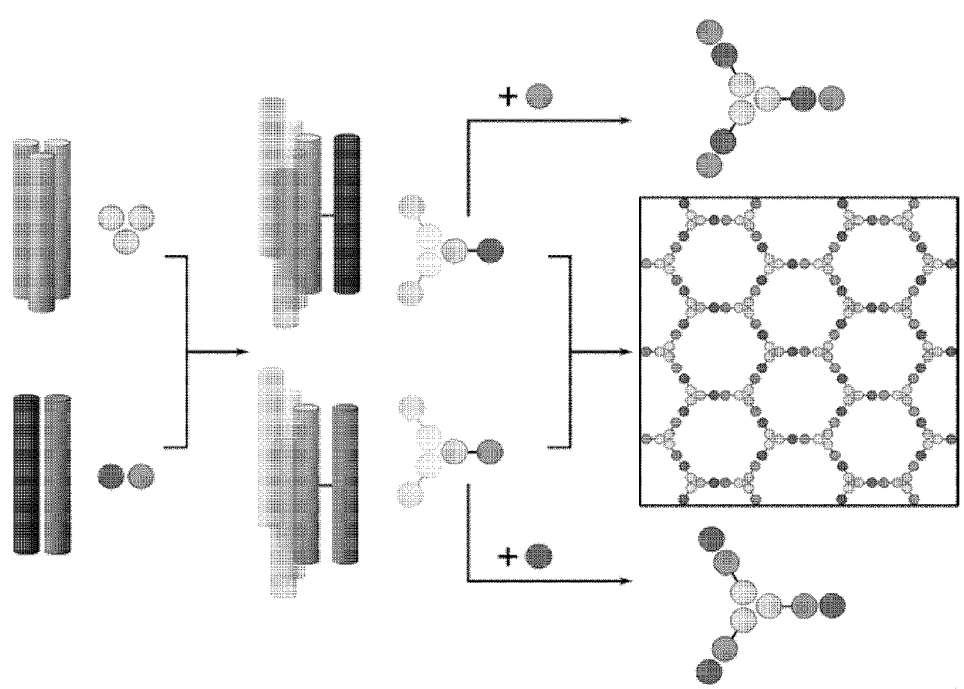
FIG. 1 shows schematically the design and self-assembly of peptide-based cages. Left to right: Homotrimeric coiled coil (CC-Tri3,) and heterodimeric coiled coils (CC-Di-AB); the latter comprises CC-Di-A and CC-Di-B. CC-Tri and CC-Di-AB are linked via asymmetric disulfide bonds to render hub A and hub B. Mixing hub A with CC-Di-B, or hub B with CC-Di-A produces discrete 9-helix assemblies; whereas, mixing the hubs directly produces a hexagonal network, which should close.

Materials—Rink amide ChemMatrix™ resin was obtained from PCAS Biomatrix Inc. (St-Jean-sur-Richelieu, Canada); Fmoc-L-amino acids and 2-(1H-benzotriazol-1-yl)-1,1,3,3-tetramethyluronium hexafluorophosphate (HBTU) were obtained from AGTC Bioproducts (Hessle, UK); 2,2'-Dipyridyldisulfide (DPDS) was obtained from Sigma-Aldrich (Gillingham, UK; all other reagents were obtained from Fisher (Loughborough, UK)).

Solid-phase assembly—Peptides were synthesised on 0.1 mmol scales on Rink amide resin using a Liberty™ microwave peptide synthesiser (CEM; Mathews, N.C., U.S.A.) employing Fmoc solid-phase techniques (25) and systematically repeated steps of coupling and deprotection interspaced with washings (5×7 mL dimethylformamide (DMF)). Coupling: Fmoc-amino acid (5 eq.), HBTU (4.5 eq.), diisopropylethylamine (10 eq.), in DMF (7 mL) for 5 min with 20 W microwave irradiation at 75° C. Deprotection: 20% piperidine in DMF for 5 min with 20 W microwave irradiation at 75° C.

Cleavage and work-up—Following linear assembly, each peptide was acetylated (acetic anhydride (3 eq.), DIPEA (4.5 eq.) in DMF (7 mL) for 20 min), and then cleaved from the resin with concomitant removal of side-chain protecting groups by treatment with a cleavage cocktail (10 mL) consisting of trifluoroacetic acid (TFA; 95%), triisopropylsilane (2.5%) and $H_2O$ (2.5%) (an additional 2.5% 1,2-ethanedithiol was also added for Cys(Trt)-containing peptide) for 3 h at room temperature. Suspended resin was removed by filtration, the peptide precipitated in ice-cold $Et_2O$, centrifuged, the pellet dissolved in 1:1 $MeCN/H_2O$, and freeze-dried. Purification was performed by RP-HPLC using a Kromatek (semi micro, 5 μm, 100 Å, 10 mm ID×150 mm L) C18 reverse phase column. Eluents used were 0.1% TFA in $H_2O$ (A) and 0.1% TFA in MeCN (B); the peptides were eluted by applying a linear gradient (at 3 mL/min) of 20% to 80% B over 40 min. Fractions collected were examined by MALDI-TOF mass spectrometry and those found to contain exclusively the desired product were pooled and lyophilized. Analysis of the purified final product by RP-HPLC indicated a purity of >95%. Successful synthesis was confirmed by MALDI-TOF mass spectrometry.

Disulfide-bond formation—The formation of an unsymmetric disulfide between CC-Tri-Cys and CC-Di-A-Cys or CC-Di-B-Cys was performed using the method of 2,2'-Dipyridyldisulfide (DPDS)-mediated thiol activation described by Ruizgayo et al., (Tetrahedron Lett., 29, 3845, 1988). Briefly, 10 mg CC-Tri3-Cys (3.8 μmoles) was dissolved in 10 mL $H_2O$ to which 10 eq. DPDS (8.4 mg) in MeOH (1 mL) was added. After 1 h, unreacted DPDS was removed by extraction with $Et_2O$ (3×20 mL), the aqueous fraction freeze-dried, and the "thiol-activated" CC-Tri3-Cys (SPy) purified by RP-HPLC and successful synthesis confirmed by MALDI-TOF mass spectrometry. Next, formation of unsymmetric disulfide bonds was achieved by combining solutions of CC-Tri3-Cys(SPy) (1.0 μmol, 2.8 mg in 2.8 mL $H_2O$) with CC-Di-A-Cys (1.0 μmol, 2.8 mg in 2.8 mL $H_2O$) to give CC-Tri3—CC-Di-A, with or CC-Di-A-Cys (1.0 μmol, 2.8 mg in 2.8 mL $H_2O$) to give CC-Tri3—CC-Di-B. Analysis of the purified final product by RP-HPLC indicated a purity of >95%. Successful synthesis was confirmed by MALDI-TOF mass spectrometry.

Circular Dichroism Spectroscopy

Structural analysis and Thermal Stability—CD spectra were obtained using a JASCO J-810 spectropolarimeter fitted with a Peltier temperature controller. Peptide concentrations were determined by UV absorption at 280 nm ($\epsilon_{280}$,Trp=5690 $mol^{-1}$ $cm^{-1}$; $\epsilon_{280}$,Tyr=1280 $mol^{-1}$ $cm^{-1}$) (27). Solutions were prepared in phosphate buffered saline (PBS; 137 mM NaCl, 2.7 mM KCl, and 10 mM phosphate buffer) at pH 7.4, and examined in 1 mm (100 μM, 50 μM, and 30 μM samples) or 5 mm (10 μM, and 5 μM) quartz cuvettes. Thermal denaturation experiments were performed by ramping temperature from 5° C. to 90° C. at a rate of 40° C./h. Full spectra were recorded at 5° C. intervals, whilst the CD at 222 nm was recorded at 1° C. intervals (1 nm interval, 1 nm bandwidth, 16 s response time). All peptides in the current study were examined both alone and as mixtures at concentrations of 50 μM for each peptide component. All raw data (in mdeg) were normalised for peptide concentration, pathlength, and number of amide bonds present to give mean residue ellipticity (MRE; deg $cm^2$ $dmol^{-1}$ $res^{-1}$). Melting temperatures were determined from the x-intercept of the second derivative plot of MRE at 222 nm versus temperature.

Probing Orthogonal Assembly—The orthogonal assembly of the homotrimer CC-Tri3 and the heterodimer CC-Di-AB was probed by examining the structure and thermal stability of the two components both alone (CC-Tri3: 50 μM; CC-Di-AB: 25 μM CC-Di-A+25 μM CC-Di-B), and as mixtures (50+25+25 μM). From these data, the theoretical average MRE of the two components (when examined alone) was plotted against the experimentally determined data obtained for the mixture with any increase in signal indicative of mismatched folding (i.e. non-orthogonal behaviour) between the two. None was observed.

Thermodynamic Analysis and Dissociation Constants of Coiled-Coil Assemblies

Dissociation constants for coiled coils CC-Tri3 and CC-Di-AB were determined. For this, a series of thermal denaturations (monitored by CD at 222 nm) were performed across a range of peptide concentrations (CC-Tri3: 100 μM, 50 μM, 30 μM, 10 μM, & 5 μM; CC-Di-AB: 100 μM, 50 μM, 30 μM, 10 μM total peptide concentration). From these datasets, the midpoints of thermal denaturation ($T_M$) were determined by plotting the second derivative of MRE versus temperature for these cooperatively folded molecules. In each case two-state transitions between the coiled coil of oligomeric state determined by analytical ultracentifucation (i.e. CC-Tri3 a homotrimeric coiled coil, and CC-Di-AB a heterodimer) and the unfolded state were assumed. Dissociation constants were then calculated by plotting the reciprocal of $T_M$s (in Kelvin) against the natural log of peptide concentration producing a linear relationship. From this, one can extrapolate to find the concentration of peptide which would produce a $T_M$ of the temperature of interest (T, e.g. 20° C., 37° C., etc.) from which the $K_d$ can be calculated. Determination of dissociation constants ($K_d$) for CC-Tri3 and CC-Di-AB differed due to the difference in their molecularity.

For self-complementary systems (e.g. CC-Tri3), the coiled coil $A_n$ of oligomer state n (in this case, n=3), dissociation may be described as:

$$A_n \leftrightarrow nA$$

$$K_d = \frac{[A]^n}{[A_n]} = \frac{[(1-\alpha)C_T]^n}{\alpha(C_T/n)} = \frac{nC_T^{n-1}(1-\alpha)^n}{\alpha}$$

Where $C_T$=total peptide concentration and α=is the fraction of coiled coil in the folded state, such that α=1 when the coiled coil is fully folded, and α=0 when fully denatured. Since at the melting temperature, $T_M$, α=½, it follows that when T=$T_M$:

$$K_d^{T=T_M} = \frac{nC_T^{n-1}(1/2)^n}{1/2} = n(C_T/2)^{n-1}$$

-continued $$K_d^{T=T_M} = 3(C_T/2)^2$$

(for a homotrimeric coiled coil)

For the case of a heteromeric assembly (e.g. CC-Di-AB), dissociation can be described as:

$$ABC \ldots X \leftrightarrow A + B \ldots + X$$

$$K_d = \frac{[A][B][C] \ldots [X]}{[ABC \ldots X]}$$

For the case, as in the present study, where each peptide is present in equal concentration: $[A]=[B]=C_T/n$ (where $C_T$ is the total peptide concentration and n is the oligomeric state, in this case n=2), it follows:

$$K_d = \frac{[(1-\alpha)C_T/(n)]^n}{\alpha(C_T/n)} = \frac{[(C]_T/n)^{n-1}(1-\alpha)^n}{\alpha}$$

Where, again, α=is the fraction of coiled coil in the folded state, such that α=1 when the coiled coil is fully folded, and α=0 when fully denatured. Since at the melting temperature, $T_M$, α=½, it follows that when $T=T_M$ $$K_d^{T=T_M} = \frac{1/2}{[(C]_T/n)^{n-1}(1/2)^n} = [(C]_T/2n)^{n-1}$$

$$K_d^{T=T_M} = C_T/4$$

(for a heterodimeric coiled coil)

Dynamic Light Scattering

Discrete Assemblies—The hydrodynamic diameter of coiled-coil modules (CC-Tri3 and CC-Di-AB), hubs (CC-Tri3—CC-Di-A and CC-Tri3—CC-Di-B) and terminated hubs (CC-Tri3—CC-Di-A+CC-Di-B and CC-Tri3—CC-Di-B+CC-Di-A) were obtained using a Malvern Zetasizer Nanoseries instrument. All samples were prepared at 50 μM concentration of each of the peptide components in PBS and data collected at 20° C. Data was analysed using the associated DTS Nano Particle sizing software with average size and standard deviation calculated from data collected across 15 replicate measurements. Data were plotted as the average curve centred about the mean particle size.

TCEP-Mediated rupture of SAGE particles monitored by DLS—The disulfide reducing agent tris(2-carboxyethyl) phosphine (TCEP) was used to cleave the disulfide linkages present in hub A and hub B peptides, leading to rupture of SAGE particles. SAGE particles were prepared by mixing CC-Tri3—CC-Di-A (hub A) and CC-Tri3—CC-Di-B (hub B) peptides (50+50 μM) in PBS (pH 7.4). After 1 hour, the suspended particles were diluted (1:5) with additional PBS and examined by DLS before the addition of a 10-fold excess of TCEP. After a further 1 hour, the reduced SAGE suspension was again examined by DLS and compared to results obtained from a mixture of discrete coiled-coil assemblies CC-Tri3 and CC-Di-AB examined alone. Data were plotted as the average curve centred about the mean particle size.

Sedimentation Equilibrium Experiments by Analytical Ultracentrifugation (AUC)

Sedimentation equilibrium experiments were conducted at 20° C. in a Beckman-Optima XL-I analytical ultracentrifuge using an An-60 Ti rotor. Solutions were prepared in PBS (pH 7.4) with peptide concentrations in the range 30-300 μM and spun at speeds in the range 20,000-60,000 rpm. Datasets were initially fitted to a single, ideal species model using Ultrascan. The partial specific volume for each of the various peptides and the solvent density was calculated using Sednterp: CC-Tri3 (0.7682 mL g$^{-1}$); CC-Di-AB (0.7580 mL g$^{-1}$); CC-Tri3—CC-Di-A (0.7511 mL g$^{-1}$); CC-Tri3—CC-Di-B (0.7737 mL g$^{-1}$); CC-Tri3—CC-Di-A+ CC-Di-B (0.7609 mL g$^{-1}$); CC-Tri3—CC-Di-B+CC-Di-A (0.7609 mL g$^{-1}$).

Scanning Electron Microscopy (SEM)

SAGE particles were produced by preparing 100 μM stocks of CC-Tri3—CC-Di-A plus CC-Tri3—CC-Di-B and CC-Tri3—CC-Di-A$_I$ plus CC-Tri3—CC-Di-B$_I$ peptides in PBS (pH 7.4), which were mixed in a 1:1 ratio. After 1 h, ~3 μL of resuspended material was transferred either directly to a carbon coated stub, or on a Whatman Nucleopore Track-Etch Membrane (0.08 μm pore size), and allowed to air dry before being sputter coated with gold/palladium (Emitech K575X) for 30 s at 150 mA, which, by extrapolation from data provided by the manufactures, yields a ~5 nm think deposition. Images were obtained using a FEI Quanta 400 instrument.

Atomic Force Microscopy (AFM)

SAGE particles were produced from 100 μM stocks of CC-Tri3—CC-Di-A and CC-Tri3—CC-Di-B peptides in PBS (pH 7.4), which were combined in a 1:1 ratio. 10 μl of SAGE solution was allowed to deposit onto cleaved muscovite mica for 5 minutes, before being rinsed with double-distilled H$_2$O and dried with a flow of nitrogen. Images were obtained using a Bruker Multimode AFM with Nanoscope V controller in ambient conditions in tapping mode. The cantilevers used were Bruker SNL-10 silicon nitride cantilevers (resonance 56 kHz, spring constant 0.24 N/m, nominal tip radius 2 nm).

Lateral Molecular Force Microscopy (LMFM)

The recently developed lateral molecular force microscope (LMFM) is a hybrid scanning probe technique which operates in a non-contact regime. The system utilises a scattered evanescent wave (SEW) detection system. An evanescent field is generated above the substrate/imaging-medium interface via total internal reflection of a laser beam through a high NA objective lens (Nikon, N.A=1.49; see below). When a vertically oriented cantilever (VOC) is tens of nanometres from the substrate, the tip interacts with the EM-field resulting in propagating light, which is then collected on a photo-detector. The exponential decay of the evanescent field provides a direct relationship between the intensity of scatter and the tip-substrate separation. This is used as a feedback mechanism. This optical feedback has a lateral resolution comparable to the scattering area of the cantilever tip and therefore selectively detects only local changes in the evanescent field.

The visco-elastic response of the water layers between the tip of a VOC and the sample measurably changes the resonant dynamics of the cantilever. If the VOC is now set in oscillation, at or close to its resonant frequency, then it becomes possible to simultaneously detect the short-range (i.e. <2 nm) lateral shear force and the optical signal, with the latter being used in feedback for separation control. Owing to the fact that this feedback does not adjust the height to account for the molecular roughness of the surface, this mode of operation will result in a shear force mapping of the surface at constant height. It is important to mention that this mapping will have the lateral resolution typical of the shear force microscopy, i.e., 1-2 nm. By varying the scattered intensity set-point, one can adjust the "scanning plane" much like the focal plane of an optical microscope with no damage to the sample with the microscope operating in a non-contact regime. LMFM images of λ-DNA have demonstrated optical feedback control of the vertical position of the tip to have better than 1 nm accuracy.

The SEW detection system is not detrimentally effected by a liquid environment. 4 µl of the SAGE solution described was deposited onto a glass substrate in situ on the LMFM and diluted with an additional 30 µl of PBS. This prevented the drying-induced collapse that was observed in tapping mode AFM images with its greater normal forces. The silicon nitride VOC used was designed specifically for the LMFM (Resonance$_{air}$ 380 kHz, Resonance$_{liquid}$ 67 kHz, Spring constant 0.047 N/m) and then manufactured by Nu Nano (Bristol, UK). By scanning above the sample and slowly lowering the scanning plane, the tops of the assemblies were observed in a non-contact regime revealing an expected ultra-structure. When multiple assemblies are observed in the same image without contacting the VOC, they are the same height to within the range of shear force interaction.

LMFM images produced in this study were recorded after mixing hub A and hub B in PBS, pH 7.4, and incubating at 20° C. for 1 hour. The final concentrations of these samples were 50 µM in each of the component peptides, CC-Tri3—CC-Di-A and CC-Tri3—CCDi-B, i.e. 16.66 µM of each hub. LMFM non-contact scanning investigated the SAGEs in a hydrated state, without the drying induced collapse observed in AFM scanning. For LMFM measurements 2 µl of SAGE solution was deposited onto a glass coverslip and diluted with 30 µl PBS.

Molecular Dynamics

System setup: Idealized coiled-coil dimers and the hub trimer were created with the peptide sequences of the invention (including the acetyl N-cap and amido C-capping residues) using standard coiled-coil parameters for the creation of coiled-coil structures. These were made into planar hexagonal arrays using PyMol before the disulfide bonds were added. Two arrays were constructed, comprising seven hexagons (7-Hex) and nineteen hexagons (19-Hex), respectively. Hydrogen atoms were added consistent with pH 7 and parameterised with the AMBER-99SB-ildn forcefield. Each complex was surrounded by a box 2 nm (7-Hex) and 4 nm (19-Hex) larger than the polypeptide in each dimension, and filled with TIP3P water. Random water molecules were replaced by sodium and chloride ions to give a neutral (uncharged overall) box and an ionic strength of 0.15 M. Each box (7-Hex, 614,113 atoms; 19-Hex, 2,440,958 atoms) was subjected to 10,000 steps of energy minimisation prior to the molecular dynamics simulations.

Simulation details: All simulations were performed as NPT ensembles at 298 K using periodic boundary conditions. Short range electrostatic and van der Waals' interactions were truncated at 1.4 nm while long range electrostatics were treated with the particle-mesh Ewald's method and a long range dispersion correction applied. Pressure was controlled by the Berendsen barostat and temperature by the V-rescale thermostat. The simulations were integrated with a leap-frog algorithm over a 2 fs time step, constraining bond vibrations with the P-LINCS method. An initial 200 ps simulation was performed in each case with the peptide heavy atoms restrained to their initial coordinate positions to relax the system. During the unrestrained production phase, structures were saved every 0.1 ns for analysis. Five repeats with different starting positions (corresponding to time points 100, 120, 140, 160, 180 from the position-restrained trajectories) and different random initial velocities were performed for the 7-Hex case. Simulation data were accumulated on several HPC machines including BlueCrystal (Bristol) and Iridis3 (Southampton). Data production was 3.9 ns per day on 120 cores for 7-Hex and 2.2 ns per day on 240 cores for 19-Hex on Iridis3, for example.

Analysis: Curvature at the central hexagon of 19-Hex—Hexagonal-side distances were calculated for the inside and outside faces of the central hexagonal unit for time points as follows. The centres of coordinates of the N-terminal and C-terminal heptads of the three component peptides of each hub vertex were determined by averaging these coordinates. This gave six vertices for the inside and six for the outside faces allowing the average edges to be calculated.

Figure 3:
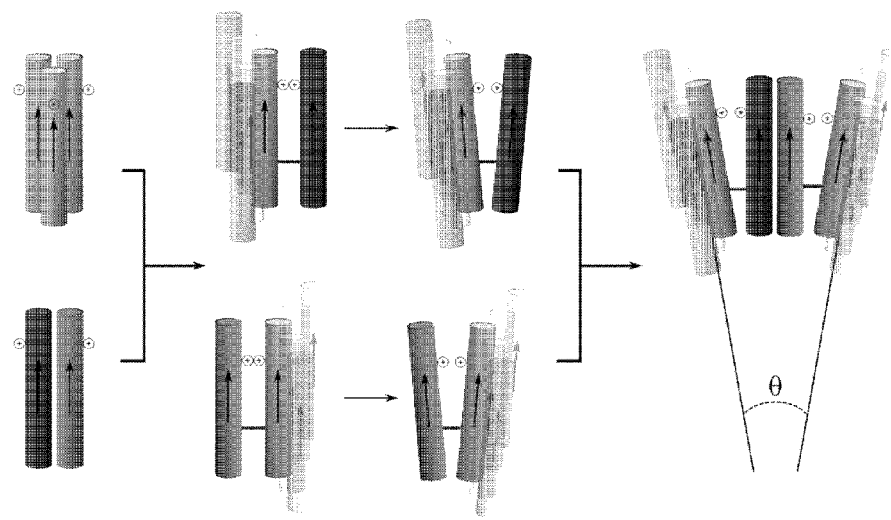
FIG. 3 shows a Schematic representation of hub splaying: α-helices are depicted as cylinders with an arrow pointing from the C-to-N-terminus. Lysine residues are present on the external surface (i.e., the f-position nearest the N-terminus) of CC-Tri3 (green) and CC-Di-AB (red/blue). Linking the coiled coils together by way of a Cys-Cys disulfide bond (purple), located fractionally towards the C-terminus, brings pairs of these lysine residues in contact. Due to the positive charges this produces a repulsion and, thus, deviation of hubs out of the plane and places the N-terminus on the "outside" of a curved surface. θ describes the angle of adjacent hubs relative to each other.

Acquisition of curvature in 7-Hex—A direction vector was calculated for each hub based on the centres-of-coordinates determined above, pointing from the C-terminus to the N-terminus. The average vector for a structure was calculated from these, followed by the angle between each hub vector (see FIG. 3). In turn, these angles were averaged to give a single value for the average splaying of the hubs at each time point. These data are plotted for the 7-Hex simulation (data not shown).

Software: The GROMACS-4.5.5 suite of software was used to set up and perform the molecular dynamics simulations. Molecular graphics manipulations and visualisations were performed using PyMol-1.5.0.1, VMD-1.9.1 and Chimera-1.6.2.

DETAILED DESCRIPTION OF THE INVENTION

Previously, we developed a toolkit of coiled coils comprising homo-dimer, trimer and tetramers, and a number of heterodimers. These synthetic peptides, of ≈30 residues in length, assemble reversibly and form stable structures at micromolar to nanomolar concentrations. To expand this toolkit and to ease the construction of the building blocks for the SAGE design, we engineered two new coiled-coil modules: a shorter (~20 residues) homotrimer (CC-Tri3), and a similarly short obligate heterodimer (CC-Di-AB) comprising acidic (CC-Di-A) and basic (CC-Di-B) sequences (see FIG. 2). We chose a heterodimer for the second module to give control in the following self-assembly process. Our goal was to link copies of CC-Tri3 and CC-Di-A or CC-Di-B through their external surfaces via disulfide bonds (FIG. 1). These covalent constructs, dubbed CC-Tri3—CC-Di-A and CC-Tri3—CCDi-B, should assemble into complementary trimeric hubs, hub A and hub B, respectively. Alone, these should be water-soluble, discrete, partly folded helical structures; i.e., CC-Tri3 should spontaneously assemble, leaving CC-Di-A and CC-Di-B orphaned on the outside of the assemblies. Upon mixing, however, the two hubs should co-assemble via association of the CC-Di-A and CC-Di-B modules to produce hexagonal networks with pores of ≈5-6 nm. Because the hubs are flexible and to maximize coiled-coil interactions, we argue that these networks should fold to form closed objects, i.e., SAGEs.

The two coiled coils were synthesized and characterized in solution using a combination of circular dichroism (CD) spectroscopy to measure secondary structure, stability, and dissociation constants ($K_d$ values); dynamic light scattering, and analytical ultracentrifugation to probe peptide association. These methods confirmed CC-Tri3 as a highly helical trimeric assembly, with concentration-dependent folding ($K_d$,20° C.=3.99×10$^{-14}$ M$^2$), and a midpoint of thermal unfolding ($T_M$) of 65° C. at 50 μM peptide. Similarly, CC-Di-A and CC-Di-B alone were unfolded in the micromolar range, but co-assembled when mixed to form a helical heterodimer, CC-Di-AB, ($K_d$,20° C.=5.83×10$^{-8}$ M; $T_M$=51° C.). We verified that CC-Tri3 and CC-Di-AB did not form mixed species in the presence of each other by showing that the melting profile of the two coiled coils, when mixed, was the same as the average of the two independent profiles (data not shown).

Building toward hubs A and B, the two-peptide constructs CC-Tri3—CC-Di-A and CC-Tri3—CC-Di-B had reduced mean residue ellipticities (MREs) compared with CC-Tri3 alone. Moreover, these values were close to averages of CC-Tri3 plus either CC-Di-A or CC-Di-B, respectively. In addition, the melting curves for the hubs were near simple averages of the component curves. Next, we mixed three equivalents of CC-Di-A with hub B, and of CC-Di-B with hub A; i.e., equimolar amounts of the underlying peptide components CC-Di-A and CC-Tri3—CC-Di-B, and of CC-Di-B and CC-Tri3—CC-Di-A. In both cases, this should produce "terminated", 9-helix assemblies (FIG. 1). Indeed, the increased MREs observed were indicative of near-complete folding of all of the modules. Moreover, the thermal denaturation curves for these assemblies were sigmoidal, and the apparent $T_M$ values measured were near the theoretical value for fully decoupled folding of the CC-Tri3 and CC-Di-AB components of 55° C. (data not shown). In all of these cases, DLS showed that the particle sizes of the peptide modules, hubs and terminated assemblies were ≈2-5 nm, consistent with discrete and appropriately sized objects. AUC gave solution molecular weights consistent with the compositions of each of the assemblies (data not shown); except for the terminated hub B, which had a mass higher than expected, but nonetheless was still a discrete assembly.

These findings all corroborate the modular design approach that underpins the SAGE concept.

When hub A and hub B were mixed in an equimolar ratio a fine white precipitate formed within minutes, accounting for the >90% of peptide initially in solution. Fresh samples diluted fivefold in PBS and analyzed by DLS indicated particles of hydrodynamic diameter 132±42 nm. The role of the disulfide linkage in the assemblies was confirmed by adding the disulfide reducing agent TCEP to the suspension. This ruptured the particles producing smaller structures of diameter 2.3±0.9 nm similar to that observed for a mixture of CC-Tri3 and CC-Di-AB (2.5±0.6 nm).

Figure 8:
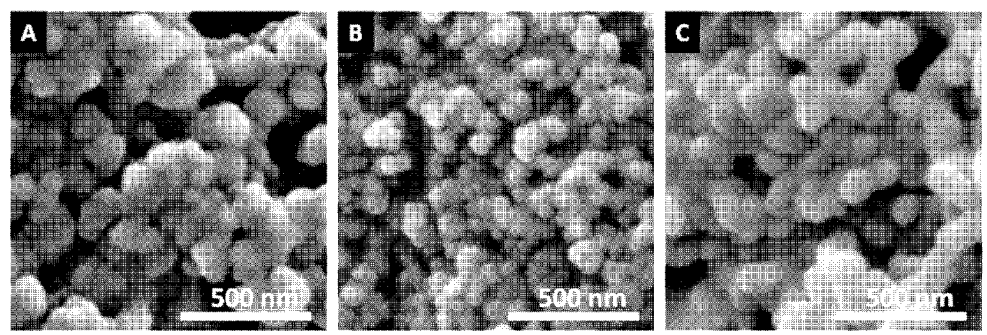
FIG. 8 shows scanning electron microscope images for SAGE particles formed by mixing CC-Tri3—CC-Di-A and CC-Tri3—CC-Di-B. B: Smaller sage particles formed by increasing the "edge penalty" energy i.e. peptides CC-Tri3—CC-Di-$A_I$ and CC-Tri3—CC-Di-$B_I$ C: Larger SAGE particles formed by decreasing local curvature i.e. peptides CC-Tri3—CC-Di-$A_O$ and CC-Tri3—CC-Di-$B_O$.

Scanning electron microscopy (SEM) revealed closed spherical objects of similar diameter (97±19 nm, n=135) (FIG. 8). Although the particles appear as aggregates in these particular micrographs, they dispersed in solution and separated when deposited on porous membranes. Tapping-mode atomic force microscopy (TM-AFM) was performed on particles deposited and dried onto mica. These particles were flattened disks 9.2±1.0 nm thick (averaged from scans over 5 particles) with diameters of 95±14 nm (from 4 measurements each on 5 particles). As the coiled-coil modules are estimated to be ~3 nm in length, the observed thickness of these disks is strong evidence that, in solution, the spheres are hollow and unilamellar rather than being solid, multi-walled, or onion-like structures. That is, they collapse upon drying, presumably releasing water through pores in the assembly. This fits our concept for the SAGEs; i.e., a folded sheet comprising a hexagonal network of peptides (FIG. 1).

Lateral molecular-force microscopy (LMFM) with optical feedback was used in a non-contact regime to explore the assemblies in solution. Again, this showed approximately spherical objects (diameter 79±12 nm (n=19); height 82±16 nm (averaged from scans over 6 particles; data not shown). These dimensions are similar to those found by SEM, which should be ~10 nm larger because of the sputtered metal coating estimated from the manufacturer's technical notes to be ~5 nm thick. Moreover, and intriguingly, the LMFM revealed ultra-structure on the surfaces of the assemblies, notably clear hexagonal shapes. The edges of the hexagons averaged 7±2 nm (n=22); although such x- and y-dimensions in scanning probe microscopies are tip dependent and are not as reliable as measurements made in z.

Our observations of closed spheres with a tight size distribution, confirmed by three independent methods, is intriguing. It raises two immediate questions: How do the hexagonal networks fold and close, and why are the resulting closed structures so uniform in size?

The first question arises because rigid hexagonal networks should form flat assembles (like a graphite sheet); and closing a sphere (as illustrated by a football) cannot be achieved with hexagons alone and requires, for example, 12 pentagons. However, the coiled-coil modules and hubs of the SAGEs are more flexible, and the assemblies that they produce may tolerate imperfections required to close. Such imperfections, which are inevitable when closing such structures, could include a few mismatched hub pairings, rather than the perfect hexagonal array shown in FIG. 1.

Closing the particles may be driven by thermodynamic and geometric constraints: Regarding thermodynamics, the hubs are designed to associate with their complementary partners, which has two consequences: (1) hubs from solution co-assemble to grow the network; and (2) these expanding edges have unsatisfied coiled coils, which drive the sheets to close and satisfy as many coiled-coil interactions as possible. In terms of geometry, it is likely there is some intrinsic tendency for the hubs to prefer tripod-like structures, with arms arranged at less than 120° creating curvature. We tested these ideas computationally and experimentally as follows.

Complete SAGEs are too large for atomistic simulations, so we modeled smaller fragments of the hexagonal network. From x-ray crystal structures and standard coiled-coil parameters, we generated an array of 19 tessellated hexagons built from CC-Tri3 and CC-Di-AB modules, and with 306 chains in total. After 5 ns of molecular dynamics (MD) in water, uniform curvature was evident in both the x and y directions. This was reproducible: in this, and multiple MD simulations for smaller 7-hexagon networks, the CC-Tri3 modules remained perpendicular to the curved surface with their N-termini always facing "out".

Figure 2:
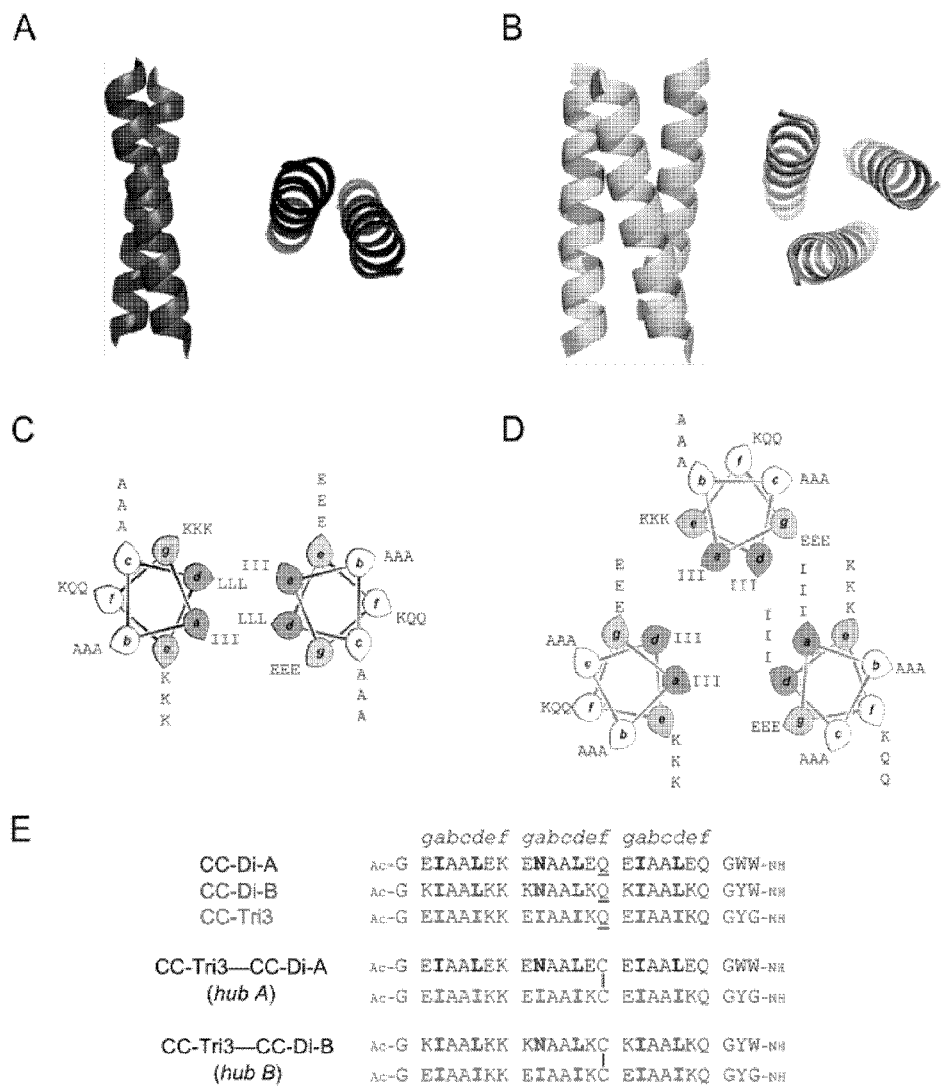
FIG. 2 shows Coiled-coil Design. The design of the coiled-coil heterodimer CC-Di-AB (model structure shown Panel A), and homotrimer CC-Tri3 (Panel B) modules for the present study was straight-forward and reflects the philosophy adopted in recent work delivering a "Basis Set" of coiled coils (Fletcher et al., 2012 supra). Hydrophobic residues occupying the central core of each coiled coil were selected to confer oligomeric state: i.e. an all-Ile core for the designed trimer (D); and an Ile/Leu core with a single Asn residue for the designed heterodimer (C) (see Fletcher et al., 2012 supra and Harbury et al., Science 262, 1401, 1993). Whilst residues flanking the hydrophobic seam were selected as either lysine or glutamic acid to produce charge patterns directing either heterotypic (CC-Di-AB, Panel C) or homotypic (CC-Tri3, panel D) assemblies. Background residues (i.e., those not found at the coiled-coil interface) were filled in with agnostic, helix-favoring residues (e.g., Ala) and finally, C-terminal Trp/Tyr tags were added to give each peptide a unique mass and chromophore signature. Sequences are provided in Panel E (from top to bottom: SEQ ID NOS. 21, 22, 23, 3, 1, 4 and 1). Once these individual modules were thoroughly characterised Gln15→Cys15 mutants were prepared and an unsymmetric Cys-Cys disulfide formed between the central f sites of the homotrimer and each of the heterodimeric peptides (Panel F). This gave a pair of back-to-back constructs ready for hub assembly.

A sphere of diameter 100 nm has a girth of ≈314 nm, corresponding to ≈40 equatorial hexagons. Thus, each hexagon is required to be wedge-shaped subtending an angle of ≈10° at the center of the sphere. Further examination of the MD trajectories, and retrospective inspection of the designed sequences suggest a molecular interpretation for this wedging: The disulphide bridges linking the coiled coils are slightly offset towards the C-termini; and each peptide has a positively charged lysine residue at the f site between these bridges and the N-termini (FIG. 2). As borne out by the MD, the positively charged lysine residues repel each other, while the disulfide bonds act as a tether. The overall effect is to splay the collective N-termini of each coiled-coil unit apart resulting in wedge-shaped hubs, producing local and then global curvature.

The question regarding the tight size distribution of the SAGEs is more difficult to rationalize, though this is likely to involve elements such as hub rigidity, the proportion of imperfections required to close a sphere, and entropic factors. To examine how hub rigidity and any preferred local curvature may vary, we analyzed multiple MD simulations of 7-hexagon tessellates from different starting conditions. After 10 ns simulations, the hub-hub angle approached equilibrium settling to 33.9±17.2°. The simulations overestimate the local, and therefore, global curvature. Nonetheless, the 10° angle estimated from the experiments is sampled in the simulations.

To exploit this apparent flexibility, and to test the importance of burying unsatisfied edges en route to closure, we attempted to engineer smaller SAGE particles. We prepared an additional heterodimer module, CC-Di-A$_I$B$_I$ (Table 2). In these peptides, Asn→Ile mutations were made at complementary a sites in the hydrophobic face to give a variant with more than two orders of magnitude higher affinity than the CC-Di-AB parent; otherwise, we do not expect this change to alter coiled-coil or hub structure or geometry. Thus, the free-energy penalty associated with unsatisfied edges, and proposed to drive closure, should be higher for the variant. When compared by SEM, the parent SAGE particles had diameters of 97±19 nm (n=135), whereas those incorporating the variant had diameters of 68±12 nm (n=97) (p<0.001). This translates to the latter having about half the surface area, and provides strong evidence that satisfying coiled-coil interactions on the edge of a growing disk is a key driving force in closing assemblies. Moreover, it illustrates another advantage of our modular design strategy; namely, that altering the $K_d$ of the individual coiled coils can be used to control SAGE size.

The SAGE concept, though inspired by natural examples, offers routes to closed systems of reduced complexity with the potential for encapsulation. Because the components are modular, interchangeable, and bear termini and side chains that could be derivatized, it should be possible to tune their properties for applications such as vehicles for drug and biomolecule delivery, cages for trapping functional enzyme cascades that allow flux of starting materials and products, components of sensing systems, and as new frameworks for the development of protocells.

Alternative Design 1: Square Lattices

Figure 4:
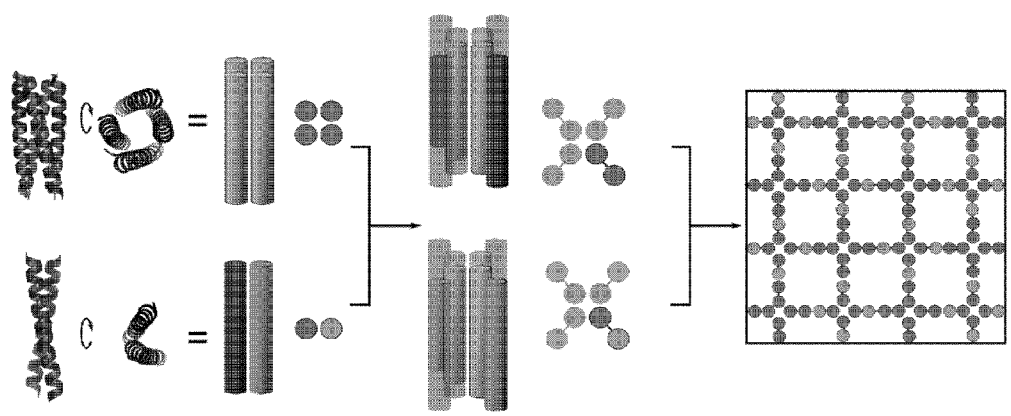
FIG. 4 shows a schematic representation for designed square lattices produced by linking homotetramer and heterodimer peptides.

We have explored the possibility of forming SAGE particles from square lattices. This design is somewhat different from the parent SAGE particles and has seen us take a homotetramer (ostensibly the same sequence as described in Fletcher et al., (Fletcher et al., ACS Synth. Biol. 1, 240 (2012)) and link it to the same heterodimer sequence as used in the parent SAGE system. This design is presented in schematic form in FIG. 4.

Peptides were synthesised and linked together in a similar fashion to that described in the first generation system. Peptide sequences are provided in table 1.

TABLE 1

Sequences of peptides designed to form square lattices. A 4 heptad tetramer sequence (CC-Tet4) is linked by a sidechain-to-sidechain asymmetric disulfide to a 3 heptad heterodimer (CC-Di-AB).

| CLASS | NAME | SEQUENCE gabcdef gabcdef gabcdef gabcdef |
|---|---|---|
| "Square lattices" | CC-Tet4-CC-Di-A | Ac-G ELAAIKQ ELAAIKK ELAAIKC ELAAIKQ GAG-NH<br>|<br>Ac-G EIAALEK ENAALEC EIAALEQ GWW-NH |
| | CC-Tet4-CC-Di-B | Ac-G ELAAIKQ ELAAIKK ELAAIKC ELAAIKQ GAG-NH<br>|<br>Ac-G KIAALKK KNAALKC KIAALKQ GYW-NH |

NOTE:
A three heptdad variant of the tetramer sequence shown above was found to produce a trimer.

Figure 5:
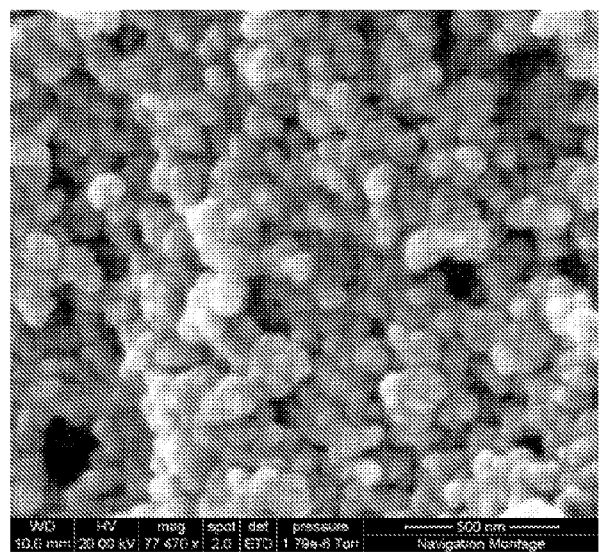
FIG. 5 shows the scanning electron microscope image for the SAGE particles produced using the square lattice structure.

Mixing CC-Tet-4—CC-Di-A & CC-Tet-4—CC-Di-B (50+50 μM in PBS) gave a fine white precipitate over the course of several minutes. The material was analysed by Scanning Electron Microscopy (see FIG. 5).

Alternative Design 2: Heterohexamer/Homodimer Assemblies

Figure 6:
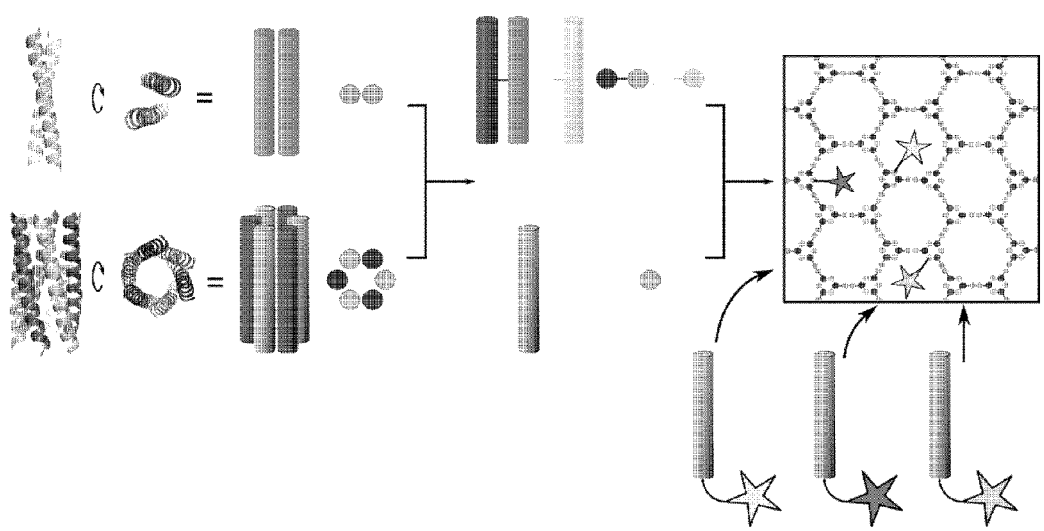
FIG. 6 shows a tessellated hexagonal network produced by an alternate architecture consisting of a homodimer and heterohexamer coiled coils. This design allows analogues of one of the heterohexamer constituent peptides to be produced by molecular biology techniques allowing a variety of additional tags or proteins (stars) to be presented on the surface of the cage.

In this design we use a heterohexamer (Zaccai et al., Nature Chemical Biology 7 935-941 (2011)), (FIG. 6), as the three-fold symmetry element in conjunction with a homodimer (such as that described in Fletcher et al (Fletcher et al., ACS Synth. Biol. 1, 240 (2012)), we can produce a system capable of forming an extended network of tessellated hexagons. The advantage of this design is that one of the heterohexamer components need be added as a simple linear peptide. Without the need to form an unsymmetric side chain-to-side chain linkage between two peptides as in the original design, we can readily make use of molecular biology techniques to decorate the surface of the SAGE particles formed. Indeed a variety of different proteins (or other small molecules), represented by stars in FIG. 6 could be incorporated into the assembly.

Alternative Design 3: Helix-Turn-Helix Variants

Figure 7:
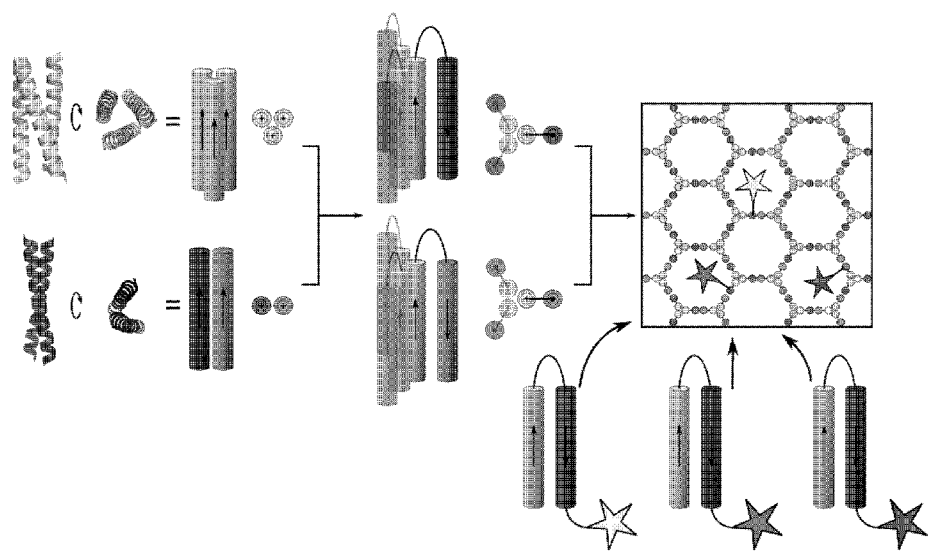
FIG. 7 shows a variant of the parent SAGE system in which the two components (i.e. the heterodimer and the homodimer) are linked together as a single, linear construct to give complementary helix-turn-helix arrangement of peptide modules. This design allows the components to be prepared by molecular biology techniques, including the ability to tag an assortment of proteins or peptides of interest to the exterior surface of the SAGE particle.

Whilst, potentially, using similar building blocks to those utilised in the parent SAGE assemblies, this strategy, like Alternative Design #2, opens the possibility of utilizing molecular biology techniques for the synthesis of additional components. In this design, the homotrimer is linked to the heterodimer peptides by way of a flexible linker producing two long helix-turn-helix peptides which can self-associate to produce a network of tessellated hexagons. This design is summarised in FIG. 7.

Studies on Size of Particles

Analogues of the peptides first used to produce SAGE particles were synthesized to determine if it is possible to increase and decrease the size of the particles. To increase the curvature, analogues were produced which made use of a more stable heterodimer (thus increasing the energy associated with the unsatified "edge") which we reasoned would give rise to smaller SAGE particles. In contrast, to decrease the curvature of the network we removed the positively charged lysine residues on the exterior surface of the coiled coils, replacing them with Glutamine residues which have the potential to form hydrogen bonds; most importantly though, they are not repulsive. We reasoned this second modification would see a decrease in local curvature and thus an increase in the size of the SAGE particles.

In addition, the inventors have also shown that it is possible to use several of the "functionalised" hubs in conjunction. For instance: parent sequences, tetralysine variants, and fluorescent peptides at once.

Methods:

Synthesis of these peptides was performed in an identical fashion to that detailed above. The cationic peptide sequences simply have an addition KKKKGG (SEQ ID NO. 19) appended to their N-terminus.

Fluorescent peptides were prepared by manual coupling of 5(6)-Carboxyfluorescein (Novabiochem) as the final, N-terminal residue. To form cages, peptides were mixed together in ratios as indicated.

Peptide Sequences

TABLE 2

Parent peptides and modified analogues used in this study to produce SAGE particles of varying size.

| CLASS | NAME | SEQUENCE gabcdef gabcdef gabcdef | SAGE particle size by SEM (nm) |
|---|---|---|---|
| "Parent Peptides" | CC-Tri3-CC-Di-A | Ac-G EIAAIKK EIAAIKC EIAAIKQ GYG-NH (SEQ ID NO: 1)<br>|<br>Ac-G EIAALEK ENAALEC EIAALEQ GWW-NH (SEQ ID NO: 3) | 97 ± 19 |
| | CC-Tri3-CC-Di-B | Ac-G EIAAIKK EIAAIKC EIAAIKQ GYG-NH (SEQ ID NO: 1)<br>|<br>Ac-G KIAALKK KNAALKC KIAALKQ GYW-NH (SEQ ID NO: 4) | |
| Smaller SAGEs by: Increasing edge penalty and, thus, curvature | CC-Tri3-CC-Di-A$_I$ | Ac-G EIAAIKK EIAAIKC EIAAIKQ GYG-NH (SEQ ID NO: 1)<br>|<br>Ac-G EIAALEK EIAALEC EIAALEQ GWW-NH (SEQ ID NO: 5) | 68 ± 12 |
| | CC-Tri3-CC-Di-B$_I$ | Ac-G EIAAIKK EIAAIKC EIAAIKQ GYG-NH (SEQ ID NO: 1)<br>|<br>Ac-G KIAALKK KIAALKC KIAALKQ GYW-NH (SEQ ID NO: 6) | |
| Larger SAGEs by: Decreasing local and thus, global curvature | CC-Tri3-CC-Di-A$_Q$ | Ac-G EIAAIKQ EIAAIKC EIAAIKQ GYG-NH (SEQ ID NO: 7)<br>|<br>Ac-G EIAALEQ ENAALEC EIAALEQ GWW-NH (SEQ ID NO: 8) | 119 ± 9 |
| | CC-Tri3-CC-Di-B$_Q$ | Ac-G EIAAIKQ EIAAIKC EIAAIKQ GYG-NH (SEQ ID NO: 7)<br>|<br>Ac-G KIAALKQ KNAALKC KIAALKQ GYW-NH (SEQ ID NO: 9) | |

RESULTS: All peptides were prepared and mixed (in PBS, 50 µM) with their respective partners. In all cases a fine white precipitant was seen to form over the period of several minutes. This material was examined by Scanning Electron Microscopy (FIG. 8).

Functionalisation of SAGE Particles.

Molecular dynamic simulations indicated that the SAGE particles formed such that the N-terminus of the homotrimer coiled coiled pointed "out". The N-terminus was therefore chosen as the initial location for modification of the SAGE particles.

As discussed below, the inventors have modified the SAGE particles in 3 different ways:
(1) Added a tetralysine (KKKKGG (SEQ ID NO. 19)) tag to reduce "clumping" of SAGE particles. The rationale being that such cationic cages should repel each other and be significantly less "sticky"
(2) To aid imaging, the inventors have produced analogues possessing a Carboxyfluorescein moiety, thus enabling the visualisation of SAGE particles in solution using light microscopy.
(3) Used SAGE particles as a platform for the presentation of antigenic peptides. The inventors have prepared particles functionalised with tetanus toxoid peptide 632-651 (IDKIS DVSTI VPYIG PALNI (SEQ ID NO. 20))

In vitro conditions—Samples were prepared by mixing 10 µM solutions of the component hubs in PBS (pH 7.4) at desired stoichiometry for 1 hour at room temperature before 50 µL of each sample was transferred a 96-well imaging plate. Imaging was performed on a Leica SP5-II confocal laser scanning microscope attached to a Leica DMI 6000 inverted epifluorescence microscope employing the 488 nm line of a 150 mW Ar laser and a 63×oil lens.

Hub A:
    (SEQ ID NO: 1) G EIAAIKK EIAAIKC EIAAIKQ GYG
                                               |
    (SEQ ID NO: 3) G EIAALEK ENAALEC EIAALEQ GWW

Hub B:
    (SEQ ID NO: 1) G EIAAIKK EIAAIKC EIAAIKQ GYG
                                               |
    (SEQ ID NO: 4) G KIAALKK KNAALKC KIAALKQ GYW

K4Hub A:
(SEQ ID NO: 15) KKKKGGG EIAAIKK EIAAIKC EIAAIKQ GYG
                                                            |
    (SEQ ID NO: 3) G EIAALEK ENAALEC EIAALEQ GWW

-continued

```
K4Hub B:
(SEQ ID NO: 15)  KKKKGGG EIAAIKK EIAAIKC EIAAIKQ GYG
                                         |
        (SEQ ID NO: 4)   G KIAALKK KNAALKC KIAALKQ GYW

CBHub B:
(SEQ ID NO: 16)  (Cb)GGG EIAAIKK EIAAIKC EIAAIKQ GYG
                                         |
        (SEQ ID NO: 4)   G KIAALKK KNAALKC KIAALKQ GYW
"CB" refers to 5(6) carboxyfluorescein.
```

Figure 9:
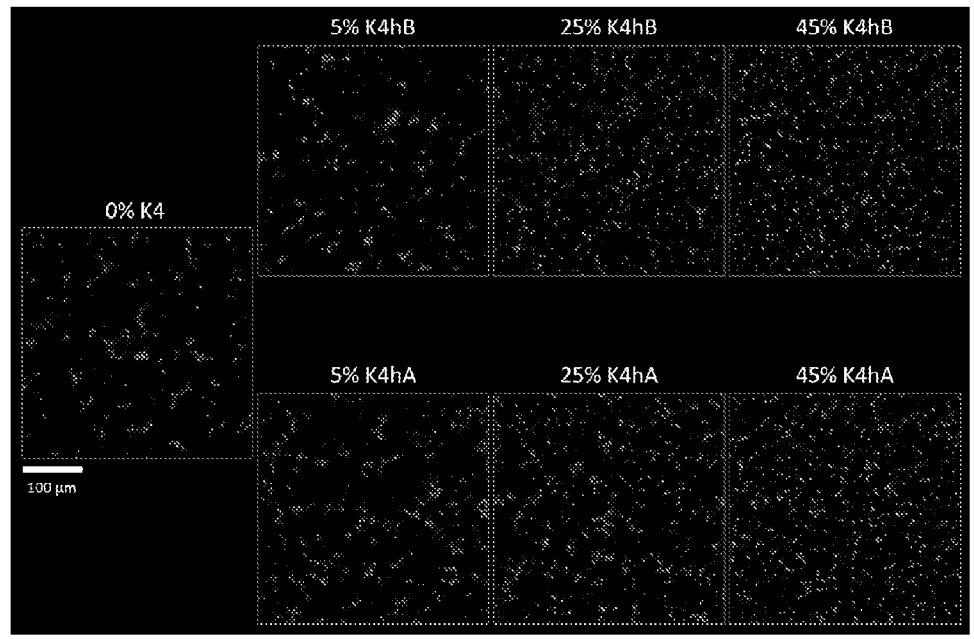
FIG. 9 shows the effects of increasing concentration of K4 tagged hub B (top) or Hub A (Bottom). Particles show increasing monodispersity and a reduced tendency to clump together as the ratio is increased. In all experiments, the fluorescent hub (Cb)Hub B was present at 5% to aid visualisation by fluorescent microscopy. "Cb" refers to 5(6)-Carboxyfluorescein.

FIG. 9 shows the effects of using such modified peptides. In these experiments acidic and basic hubs where mixed, and the ratio between K4 modified and parent sequences varied. Throughout all experiments, the fluorescent hub CBHub B was present at 5% total peptide concentration.

FIG. 9 shows that as the percentage of the K4 modified hub increased the level of clumping of the particles is reduced.

Functionalised with an Antigenic Peptide

Figure 10:
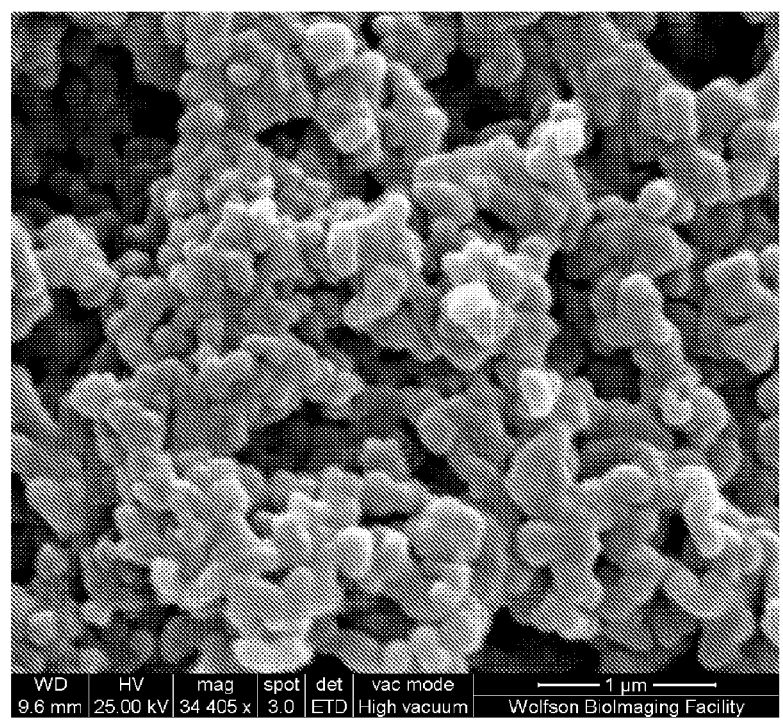
FIG. 10 shows SEM results for SAGE particles bearing the tetanus toxoid peptide 632-651 on the N-terminus of the trimer portion of Hub B. Cages were prepared by dissolving the two hub peptides in PBS and combining to give a solution containing 50+50 μM of the two peptides. After 1 hour the resultant suspension was transferred to stub and allowed to dry. Samples were sputtercoated and examined by SEM.

The inventors have also shown that peptide epitopes can be appended to the hubs without unduly affecting assembly. FIG. 10, below, shows SAGE particles functionalised with tetanus toxoid peptide 632-651. This sequence was appended to the N-terminus of the trimer sequence of Hub B (used in conjunction with the parent HubA).

The peptides were prepared, handled and analysed using the same methods as described above.

```
Hub A:
    (SEQ ID NO: 1)  G EIAAIKK EIAAIKC EIAAIKQ GYG
                                      |
    (SEQ ID NO: 3)  G EIAALEK ENAALEC EIAALEQ GWW

Hub B:
    (SEQ ID NO: 1)  G EIAAIKK EIAAIKC EIAAIKQ GYG
                                      |
IDKISDVSTIVPYIG-
PALNI GGG KIAALKK KNAALKC KIAALKQ GYW
(SEQ ID NO: 17)
```

FIG. 10 shows that the hubs correctly form SAGE peptides.

All documents mentioned above are hereby incorporated by reference.

The invention claimed is:

1. A self-assembled cage-like (SAGE) particle comprising a plurality of first hubs and a plurality of second hubs, wherein:
   i. each of the first hubs comprises a core comprising a trimeric, tetrameric or hexameric coiled coil peptide structure, wherein the core of each first hub is linked to at least 3 first peptides, wherein each first peptide is capable of interacting with a second peptide to form a dimeric coiled coil structure; and
   ii. each of the second hubs comprises a core comprising a trimeric, tetrameric or hexameric coiled coil peptide structure, wherein the core of each second hub is linked to at least 3 second peptides, wherein each second peptide is capable of interacting with a first peptide to form a dimeric coiled coil structure,
   wherein first hubs and second hubs interact by the formation of dimeric coiled core structures between first and second peptides, forming a network which closes to form a sphere with a hollow core and surface pores,
   wherein the core of each of the first and second hubs is selected from the group consisting of
   a homotrimeric coiled coil structure wherein each peptide of the trimeric coiled structure comprises SEQ ID NO: 1, 7, 15, or 16,
   a homotetrameric coiled coil structure wherein each peptide of the tetrameric coiled structure comprises SEQ ID NO: 2,
   a hexameric coiled coil structure wherein three of the peptides of the hexameric structure comprise SEQ ID NO: 10, and the other three peptides comprise SEQ ID NO: 11, and
   a heterotrimeric coiled coil structure wherein a peptide comprising SEQ ID NO: 12, a peptide comprising SEQ ID NO: 13, and a peptide comprising SEQ ID NO: 14 form the structure, and
   wherein each of the dimeric coiled coil structures are formed by a pair of first and second peptides selected from the group consisting of
      a second peptide comprising SEQ ID NO: 3 and a second peptides comprising SEQ ID NO: 4,
      a first peptide comprising SEQ ID NO: 5 and a second peptide comprising SEQ ID NO: 6.
      a first peptide comprising SEQ ID NO: 3 and a second peptide comprising SEQ ID NO: 17, and
      a first peptide comprising SEQ ID NO: 8 and a second peptide comprising SEQ ID NO: 9.

2. The self-assembled cage-like (SAGE) particle of claim 1, wherein each of the first peptides and second peptides are linked to a core via a covalent bond.

3. The self-assembled cage-like (SAGE) particle of claim 1, wherein each of the first peptides and the second peptides are linked to a core via disulfide linkages.

4. The self-assembled cage-like (SAGE) particle of claim 1, wherein each of the first peptides and second peptides are linked to a core via a flexible linker.

5. The self-assembled cage-like (SAGE) particle of claim 1, wherein the core of each of the first and second hubs comprises a homotrimeric coiled coil peptide structure or a homotetrameric coiled coil peptide structure.

6. The self-assembled cage-like (SAGE) particle of claim 1, wherein the core of each of the first and second hubs comprises a homotrimeric coiled coil peptide structure.

7. The self-assembled cage-like (SAGE) particle of claim 1, wherein the core of each of the first and second hubs comprises a homotrimeric coiled coil structure, wherein each peptide of the trimeric coiled coil structure comprises:

```
                                              (SEQ ID NO: 1)
         G EIAAIKK EIAAIKC EIAAIKQ GYG.
```

8. The self-assembled cage-like (SAGE) particle of claim 1, wherein the core of each of the first and second hubs comprises a homotrimeric coiled coil structure, wherein each peptide of the trimeric coiled coil structure comprises:

```
                                             (SEQ ID NO: 15)
       KKKKGGG EIAAIKK EIAAIKC EIAAIKQ GYG.
```

9. The self-assembled cage-like (SAGE) particle of claim 1, wherein the core of each of the first and second hubs comprises a homotrimeric coiled coil structure, wherein each peptide of the trimeric coiled coil structure comprises:

```
                                             (SEQ ID NO. 16)
    (5(6)-Carboxyfluorescein)-GGG EIAAIKK EIAAIKC

EIAAIKQ GYG.
```

10. The self-assembled cage-like (SAGE) particle of claim 1, wherein the core of each of the first and second hubs comprises a homotetrameric coiled coil structure, wherein each peptide of the tetrameric coiled coil structure comprises:

```
                                              (SEQ ID NO: 2)
       G ELAAIKQ ELAAIKK ELAAIKC ELAAIKQ GAG.
```

11. The self-assembled cage-like (SAGE) particle of claim 1, wherein each of the dimeric coiled coil structures are formed by a first peptide comprising

```
                                                    (SEQ ID NO: 3)
         G EIAALEK ENAALEC EIAALEQ GWW,
``` and comprising

```
                                                    (SEQ ID NO: 4)
         G KIAALKK KNAALKC KIAALKQ GYW.
```

12. The self-assembled cage-like (SAGE) particle of claim 1, wherein each of the dimeric coiled coil structures are formed by a first peptide comprising

```
                                                    (SEQ ID NO: 5)
         G EIAALEK EIAALEC EIAALEQ GWW,
``` and comprising

```
                                                    (SEQ ID NO: 6)
         G KIAALKK KIAALKC KIAALKQ GYW.
```

13. The self-assembled cage-like (SAGE) particle of claim 1, wherein each of the dimeric coiled coil structures are formed by a first peptide comprising

```
                                                    (SEQ ID NO: 3)
         G EIAALEK ENAALEC EIAALEQ GWW,
``` and a second peptide comprising

```
                                                    (SEQ ID NO: 17)
         IDKIS DVSTI VPYIG PALNI GGG KIAALKK KNAALKC
         KIAALKQ GYW.
```

14. The self-assembled cage-like (SAGE) particle of claim 1, wherein the core of each of the first and second hubs comprises a homotrimeric coiled coil structure, wherein each peptide of the trimeric coiled coil structure comprises:

```
                                                    (SEQ ID NO: 7)
         G EIAAIKQ EIAAIKC EIAAIKQ GYG.
```

15. The self-assembled cage-like (SAGE) particle of claim 14, wherein each of the dimeric coiled coil structures are formed by a first peptide comprising

```
                                                    (SEQ ID NO: 8)
         G EIAALEQ ENAALEC EIAALEQ GWW,
``` and a second peptide having comprising

```
                                                    (SEQ ID NO: 9)
         G KIAALKQ KNAALKC KIAALKQ GYW.
```

16. The self-assembled cage-like (SAGE) particle of claim 1, wherein the core of each of the first and second hubs comprises a hexameric coiled coil structure, wherein three of the peptides forming the structure comprise:

```
                                                    (SEQ ID NO: 10)
         GELKAIAQELKAIAKELKAIA WEDKAIAQGAGY
``` and the other three peptides comprise:

```
                                                    (SEQ ID NO: 11)
         GELKAIAQELKAIAKELKAIAWEHKAIAQGAG.
```

17. The self-assembled cage-like (SAGE) particle of claim 1, wherein the core of each of the first and the second hubs comprises a heterotrimeric coiled coil structure, wherein a peptide comprising:

```
                                                    (SEQ ID NO: 12)
         G EIAAIEQ EIAANKK EIAAIKW KIAAIKQ G,
         a peptide comprising
                                                    (SEQ ID NO: 13)
         G KIAAIKQ EIAANEK EIAAIKW EIAAIKQ G,
         and a peptide comprising
                                                    (SEQ ID NO: 14)
         G EIAAIKQ KIAANKK EIAAIKW EIAAIEQ G
``` form the heterotrimeric coiled coil structure.

18. The self-assembled cage-like (SAGE) particle of claim 1 that encapsulates a molecule.

19. The self-assembled cage-like (SAGE) particle of claim 18, wherein the encapsulated molecule is a protein, a virus, DNA or RNA.

20. The self-assembled cage-like (SAGE) particle of claim 1 wherein molecules are presented on the surface of the particle.

21. The self-assembled cage-like (SAGE) particle of claim 20, wherein the molecules are selected from molecules that target the particle to specific cell types, antigenic peptides, proteins, adjuvants, labels, cationic elements, chemically addressable functionalities for subsequently attaching other molecules, targeting moieties for targeting the SAGE particles to cell receptors, enzymes, therapeutic proteins and pharmaceutical agents.

22. The self-assembled cage-like (SAGE) particle of claim 20, wherein a molecule is provided on the N- and/or C-termini of one or more of the peptides forming the particle.

23. A method of producing a self-assembling cage-like particle according to claim 1, comprising providing a plurality of the first hubs and a plurality of the second hubs, and mixing said first and second hubs together.

24. A kit for making a self-assembling cage-like particle according to claim 1, the kit comprising a plurality of the first hubs and a plurality of the second hubs wherein upon mixing the hubs associate to form the particle.

25. A peptide having comprising one of the following sequences:

```
                                                    (SEQ ID NO: 1)
         G EIAAIKK EIAAIKC EIAAIKQ GYG;
                                                    (SEQ ID NO: 2)
         G ELAAIKQ ELAAIKK ELAAIKC ELAAIKQ GAG;
```

```
                                                   (SEQ ID NO: 3)
G EIAALEK ENAALEC EIAALEQ GWW;

(SEQ ID NO: 4)
G KIAALKK KNAALKC KIAALKQ GYW;

(SEQ ID NO: 5)
G EIAALEK EIAALEC EIAALEQ GWW;

(SEQ ID NO: 6)
G KIAALKK KIAALKC KIAALKQ GYW;

(SEQ ID NO: 7)
G EIAAIKQ EIAAIKC EIAAIKQ GYG;

(SEQ ID NO: 8)
G EIAALEQ ENAALEC EIAALEQ GWW;

(SEQ ID NO: 9)
G KIAALKQ KNAALKC KIAALKQ GYW;

(SEQ ID NO: 12)
G EIAAIEQ EIAANKK EIAAIKW KIAAIKQ G;

(SEQ ID NO: 13)
G KIAAIKQ EIAANEK EIAAIKW EIAAIKQ G;
and (SEQ ID NO: 14)
G EIAAIKQ KIAANKK EIAAIKW EIAAIEQ G.
```

26. A peptide according to claim 25, wherein a molecule is attached directly or via a linker sequence to the N-terminus or C-terminus of the peptide.

27. The peptide of claim 26, wherein the molecule is selected from molecules that target the particle to specific cell types, antigenic peptides, proteins, adjuvants, labels, cationic elements, chemically addressable functionalities for subsequently attaching other molecules, targeting moieties for targeting to cell receptors, enzymes, therapeutic proteins and pharmaceutical agents.

28. A peptide having one of the following sequences:

```
                                                  (SEQ ID NO: 15)
KKKKGGG EIAAIKK EIAAIKC EIAAIKQ GYG;

(SEQ ID NO: 16)
(5(6)-Carboxyfluorescein)-GGG EIAAIKK EIAAIKC
EIAAIKQ GYG;
and (SEQ ID NO: 17)
IDKIS DVSTI VPYIG PALNI GGG KIAALKK KNAALKC
KIAALKQ GYW.
```

29. A functionally equivalent peptide to the peptide of claim 25,
wherein the functionally equivalent peptide has at least 85% sequence identity to at least one of SEQ ID NOs: 1-9 and 12-14, and wherein the
functionally equivalent peptide retains the ability to form a multimeric structure.

30. A peptide comprising SEQ ID NO: 1 linked to a peptide comprising any one of
SEQ ID NOs: 3 to 6, wherein the peptides are linked via a disulfide linkage between cysteine residues.

31. A peptide comprising SEQ ID NO: 2 linked to a peptide comprising any one of
SEQ ID NO: 3 to 6, wherein the peptides are linked via a disulfide linkage between the cysteine residues.

32. A peptide comprising SEQ ID NO: 7 linked a peptide comprising
SEQ ID NO: 8 or 9, wherein the peptides are linked via a disulfide linkage between cysteine residues.

33. A peptide comprising SEQ ID NO: 15 linked to a
peptide comprising any one of SEQ ID NOs: 3 to 6, wherein the peptides are linked via a disulfide linkage between cysteine residues.

34. A peptide comprising SEQ ID NO: 16 linked to a peptide comprising any one of
SEQ ID NOs: 3 to 6, wherein the peptides are linked via a disulfide linkage between cysteine residues.

35. A peptide comprising SEQ ID NO: 1, 2, 15, or 16 linked to a
peptide comprising SEQ ID NO: 17, wherein the peptides are linked via a disulfide linkage between cysteine residues.

* * * * *

UNITED STATES PATENT AND TRADEMARK OFFICE
CERTIFICATE OF CORRECTION

PATENT NO. : 9,562,074 B2
APPLICATION NO. : 14/783885
DATED : February 7, 2017
INVENTOR(S) : Woolfson et al.

It is certified that error appears in the above-identified patent and that said Letters Patent is hereby corrected as shown below:

In the Claims

In Column 37, Claim 1, Line 51:
Please delete "a second peptide" and insert --a first peptide--.

In Column 37, Claim 1, Line 52:
Please delete "second peptides" and insert --second peptide--.

In Column 37, Claim 1, Line 54:
Please delete "ID NO: 6." and insert --ID NO: 6,--.

In Column 39, Claim 11, Line 6:
Please delete "comprising" and insert --a second peptide comprising--.

In Column 39, Claim 12, Line 20:
Please delete "comprising" and insert --a second peptide comprising--.

In Column 39, Claim 15, Line 58:
Please delete "peptide having comprising" and insert --peptide comprising--.

In Column 40, Claim 25, Line 59:
Please delete "peptide having comprising" and insert --peptide comprising--.

In Column 42, Claim 31, Line 25:
Please delete "between the cysteine" and insert --between cysteine--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*